(12) United States Patent
Akutsu

(10) Patent No.: US 10,150,620 B2
(45) Date of Patent: Dec. 11, 2018

(54) SAMPLE TRANSFER DEVICE AND SAMPLE PROCESSING SYSTEM

(71) Applicant: HITACHI HIGH-TECHNOLOGIES CORPORATION, Tokyo (JP)

(72) Inventor: Masashi Akutsu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 10 days.

(21) Appl. No.: 15/028,199

(22) PCT Filed: Oct. 27, 2014

(86) PCT No.: PCT/JP2014/078505
§ 371 (c)(1),
(2) Date: Apr. 8, 2016

(87) PCT Pub. No.: WO2015/064540
PCT Pub. Date: May 7, 2015

(65) Prior Publication Data
US 2016/0244269 A1 Aug. 25, 2016

(30) Foreign Application Priority Data
Nov. 1, 2013 (JP) .................................. 2013-228714

(51) Int. Cl.
*G01N 35/04* (2006.01)
*B65G 43/00* (2006.01)
(Continued)

(52) U.S. Cl.
CPC ......... *B65G 43/00* (2013.01); *G01N 35/0092* (2013.01); *G01N 35/026* (2013.01);
(Continued)

(58) Field of Classification Search
CPC ............................................. G01N 2035/041
See application file for complete search history.

(56) References Cited

U.S. PATENT DOCUMENTS

2009/0162247 A1 6/2009 Tokieda et al.
2011/0316713 A1* 12/2011 Okubo ............. G01N 35/00623
340/673
(Continued)

FOREIGN PATENT DOCUMENTS

CN 11181826 A 5/1998
CN 102027375 A 4/2011
(Continued)

OTHER PUBLICATIONS

Hawker, CD. Laboratory Automation: Total and Subtotal; Journal of Clinics in Laboratory Medicine 27 (2007); p. 749-770.*
(Continued)

*Primary Examiner* — Benjamin R Whatley
(74) *Attorney, Agent, or Firm* — Mattingly & Malur, PC

(57) ABSTRACT

A sample transfer device has sample container transfer mechanisms which are arranged between a conveyance path for conveying a sample container holder to one of plural analysis devices. A sample container housing a sample is mounted in the sample container holder. The sample container transfer mechanisms transfer the sample container between the sample container holder and a sample container rack, which is used for mounting the sample container in the analysis device and for conveyance. The sample transfer device determines whether or not an analysis device is in a state suitable for receiving the sample container, and if the analysis device is determined not to be in a state suitable for receiving, controls the sample container transfer mechanism to convey the sample container to the other analysis device via the conveyance path. In this way, it is possible to suppress delays in analysis processing and decreases in throughput.

8 Claims, 21 Drawing Sheets

(51) Int. Cl.
*G01N 35/02* (2006.01)
*G01N 35/00* (2006.01)

(52) U.S. Cl.
CPC ........ *G01N 35/04* (2013.01); *G01N 35/0099* (2013.01); *G01N 2035/0415* (2013.01); *G01N 2035/0462* (2013.01); *G01N 2035/0477* (2013.01)

(56) References Cited

U.S. PATENT DOCUMENTS

| 2012/0301358 | A1* | 11/2012 | Haechler | G01N 35/026 422/64 |
| 2014/0208872 | A1 | 7/2014 | Yasuzawa et al. | |
| 2014/0234978 | A1* | 8/2014 | Heise | B65G 54/02 436/48 |
| 2014/0294699 | A1 | 10/2014 | Akutsu et al. | |

FOREIGN PATENT DOCUMENTS

| JP | 07-092171 A | 4/1995 |
| JP | 07-280815 A | 10/1995 |
| JP | 11-281652 A | 10/1999 |
| JP | 11-316236 A | 11/1999 |
| JP | 2006-189311 A | 7/2006 |
| JP | 2009-150859 A | 7/2009 |
| JP | 2013-178161 A | 9/2013 |
| WO | 2013/042549 A1 | 3/2013 |
| WO | 2013/070756 A2 | 5/2013 |
| WO | 2013/099538 A1 | 7/2013 |

OTHER PUBLICATIONS

Extended European Search Report received in corresponding European Application No. 14858625.8 dated May 30, 2017.
International Preliminary Report on Patentability received in corresponding International Application No. PCT/JP2014/078505 dated May 12, 2016.
International Search Report of PCT/JP2014/078505 dated Jan. 27, 2016.
Chinese Office Action received in corresponding Chinese Application No. 201480053410.0 dated Sep. 5, 2016.
Chinese Office Action received in corresponding Chinese Application No. 201480053410.0 dated Feb. 22, 2017.
Japanese Office Action received in corresponding Japanese Application No. 2015-544988 dated Aug. 28, 2018.

* cited by examiner

SAMPLE TRANSFER DEVICE AND SAMPLE PROCESSING SYSTEM

TECHNICAL FIELD

The present invention relates to a specimen transfer device which transfers a biological sample, such as blood or urine, and a specimen processing system using the same.

BACKGROUND ART

In a hospital, an inspection organization, or the like, a qualitative/quantitative analysis of a biological sample, such as blood or urine, obtained from a patient by gathering blood, urine, or the like (hereinafter referred to as a specimen) is performed, and a condition of the patient is obtained from an inspection result of each inspection item based on a result of the analysis.

In recent years, it has been demanded that a series of processing, such as preprocessing or analysis processing of each specimen, is performed in large quantities in a short time accompanying the diversification of specimen inspection. A specimen processing system which automatically performs preprocessing or analysis processing is used in the qualitative/quantitative analysis of the specimen.

As such a specimen processing system, for example, PTL 1 (JP 7-280815 A) discloses an automatic specimen processing apparatus which includes a specimen loading device for containing a specimen, a preprocessing device for preprocessing the specimen from this specimen loading device, and an analysis device for analyzing the specimen from this preprocessing device and which performs preprocessing to analysis processing of the specimen.

CITATION LIST

Patent Literature

PTL 1: JP 07-280815 A

SUMMARY OF INVENTION

Technical Problem

Incidentally, there is a case where a kind/shape of a carrier which holds a specimen container containing a specimen is different among a preprocessing device, a plurality of analysis devices, and the like which configure a specimen processing system. Therefore, in such a case, it is necessary that the specimen container is transferred to the carrier corresponding to each analysis device by a transfer device provided at a portion connected with each of the plurality of analysis devices in a conveyance path for the specimen container.

However, in a case where replenishment of a reagent used for the analysis of the specimen is required or where the analysis device serving as a conveyance destination of the specimen container is brought into an unusable state by failure or the like, it is considered that the specimen container conveyed to the analysis device stagnates in the transfer device or on the conveyance path. Also, it is concerned that the analysis processing of each specimen is delayed or that throughput of the analysis processing in the entire specimen analysis system is reduced.

In consideration of the above description, an object of the present invention is to provide a specimen processing system capable of suppressing delay in analysis processing or reduction in throughput.

Solution to Problem

In order to achieve the object, the present invention is a specimen container transfer device including: a specimen container transfer mechanism part disposed between a conveyance path which conveys a first carrier mounted with a specimen container, in which a specimen is contained, to one of a plurality of conveyance destinations and the conveyance destination, the specimen container transfer mechanism part transferring the specimen container between the first carrier conveyed by the conveyance path and a second carrier used to mount and convey the specimen container at the conveyance destination; and a transfer control part which determines whether the conveyance destination is in a state suitable for receiving the specimen container, and if it is determined that the conveyance destination is in a state unstable for reception, the transfer control part controlling the specimen container transfer mechanism part so as to convey the first carrier to the other conveyance destination via the conveyance path.

Advantageous Effects of Invention

According to the present invention, delay in analysis processing or reduction in throughput can be suppressed.

DESCRIPTION OF EMBODIMENTS

Hereinafter, embodiments of the present invention will be described with reference to the drawings.

<First Embodiment>

A first embodiment of the present invention will be described with reference to FIGS. 1 to 27.

Figure 1:
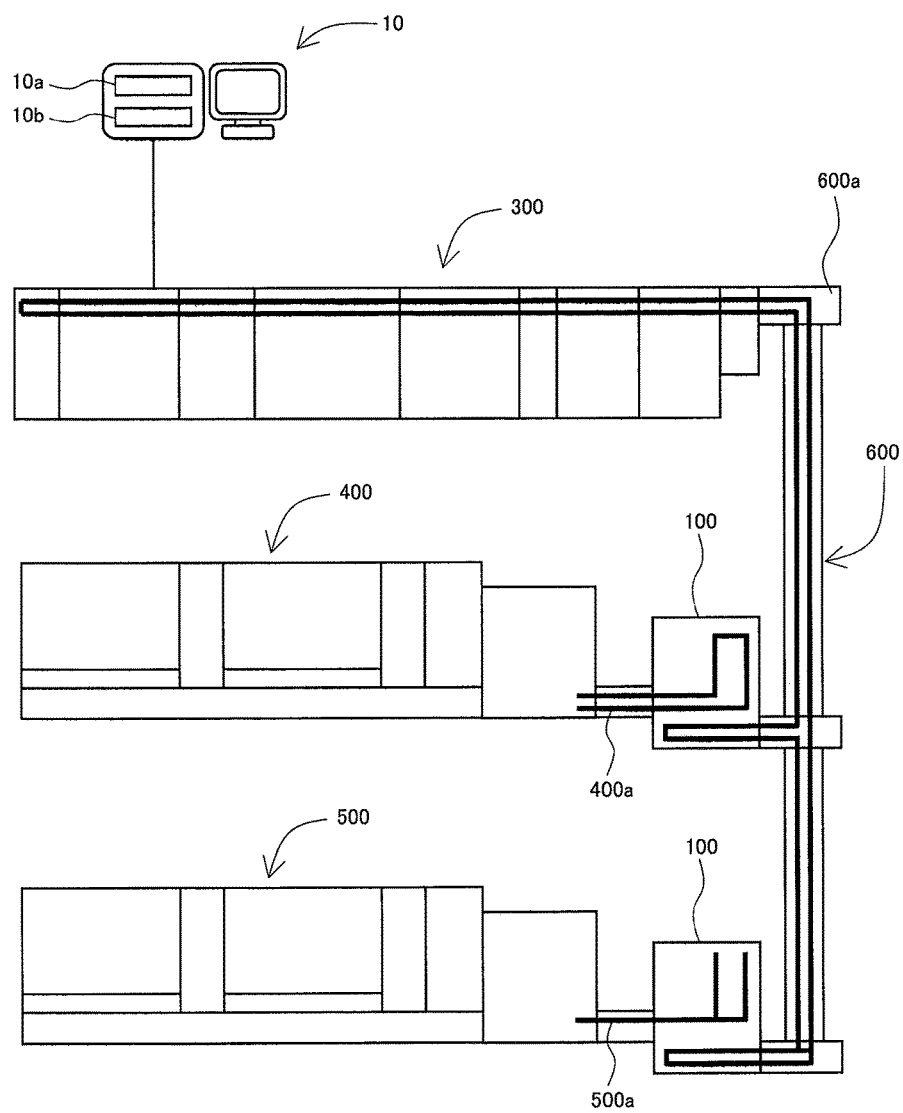
FIG. 1 is a diagram schematically illustrating an entire configuration of a specimen processing system according to a present embodiment.

FIG. 1 is a diagram schematically illustrating an entire configuration of a specimen processing system according to the present embodiment.

In FIG. 1, the specimen processing system schematically includes a preprocessing device 300, a plurality of (two in the present embodiment) analysis devices 400, 500, a conveyance path 600, a plurality of (two in the present embodiment) specimen container transfer mechanism parts 100, 200, and a control part 10. The preprocessing device 300 performs preprocessing on a specimen 1b contained in a specimen container 1 (see FIG. 3 or the like below). The analysis devices 400, 500 perform analysis processing on the specimen 1b of the specimen container 1 subjected to the preprocessing. The conveyance path 600 conveys a specimen container holder 2 mounted with the specimen container 1 (see FIG. 3 or the like below) between the preprocessing device 300 and the analysis devices 400, 500. The specimen container transfer mechanism parts 100, 200 are respectively provided between the conveyance path 600 and the plurality of (two) analysis devices 400, 500, and transfer the specimen container 1 between the specimen container holder 2 conveyed by the conveyance path 600 and a specimen container rack 3 used to mount and convey the specimen container 1 (see FIG. 4 or the like below) in the respective analysis devices 400, 500. The control part 10 controls operation of the entire specimen processing system.

It should be noted that the control part 10 has a transfer control part 10a (to be described below) and a storage part 10b. The transfer control part 10a controls operation of the specimen container transfer mechanism parts 100, 200. The storage part 10b stores specimen information, such as an analysis item or priority information, of the specimen 1b contained in the specimen container 1 to be thrown in the specimen processing system, a relationship between each identifier and the specimen 1b, and the like. The specimen container transfer mechanism parts 100, 200, the transfer control part 10a, and a portion of the storage part 10b configure a specimen transfer device.

The preprocessing device 300 is formed of a specimen throw-in part for throwing in the specimen container 1, in which the specimen is contained, a centrifugation part which performs centrifugation processing on the specimen, an opening part which opens the specimen container 1, an identification information attachment part which attaches identification information, such as a bar code, to the specimen container 1, and the like. The conveyance path 600 is disposed in the above-described respective configurations of the preprocessing device 300, and the specimen container 1 mounted on the specimen container holder 2 is conveyed by the conveyance path 600.

Figure 3:
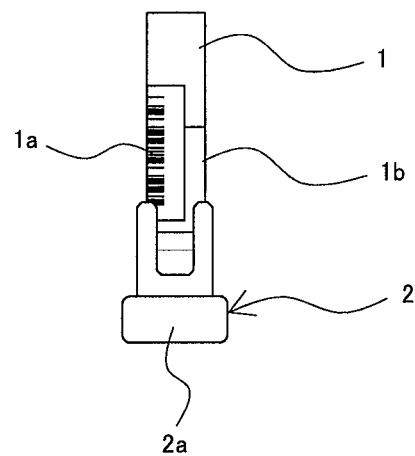
FIG. 3 is an exemplary diagram illustrating a specimen container holder used in a preprocessing device and a conveyance path together with a specimen container.

FIG. 3 is an exemplary diagram illustrating the specimen container holder used in the preprocessing device and the conveyance path together with the specimen container.

As illustrated in FIG. 3, the specimen 1b is contained in the specimen container 1, and a bar code 1a is attached to a side surface thereof as an identifier of the specimen container 1 and the contained specimen 1b. The bar code 1a can be read by bar code readers 112, 113b (to be described below).

In FIG. 3, the specimen container holder 2 used in the preprocessing device 300 and the conveyance path 600 is configured to mount the specimen container 1 one by one, and is configured so that the bar code 1a of the specimen container 1 can be recognized from a side even in a state in which the specimen container 1 is mounted on the specimen container 2.

Further, an RFID element 2a is included at a bottom part of the specimen container holder 2 as an identifier for identifying the specimen container holder 2 and can be read by an RFID reader 107 (to be described below).

Figure 4:
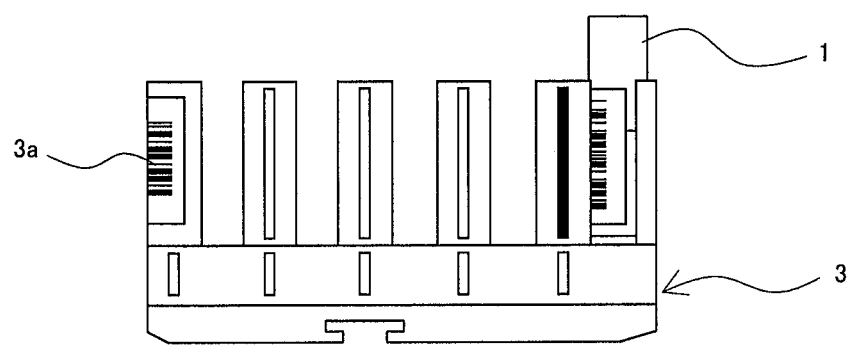
FIG. 4 is an exemplary diagram illustrating a specimen container rack used in an analysis device together with the specimen container.

FIG. 4 is an exemplary diagram illustrating the specimen container rack used in the analysis devices together with the specimen container.

In FIG. 4, the specimen container rack 3 used in the analysis devices 400, 500 is configured to mount the plurality of specimen containers 1 (five in the present embodiment).

Further, a bar code 3a is provided on a side of the specimen container rack 3 as an identifier for identifying the specimen container rack 3 and can be read by the bar code reader (to be described below).

It should be noted that, in order to simplify description, description has been given of a case where the specimen container rack 3 for mounting and conveying the specimen containers 1 in the analysis device 400 and the specimen container rack 3 for mounting and conveying the specimen containers 1 in the analysis device 500 are the same. However, the present invention is not limited to this. In other words, the present invention can be also applied to a case where specimen container racks with different shapes or specimen container racks with different numbers of mounted specimen containers 1 are used in the respective analysis devices 400, 500.

Return to FIG. 1.

The conveyance path 600 conveys the specimen container holder 2 having no self-propelled function. The conveyance path 600 is, for example, formed of a belt conveyer driven by a rotary driving device (not illustrated). Even in a state in which the plurality of specimen container holders 2 is disposed on the belt conveyor, the conveyance path 600 can simultaneously convey the specimen container holders 2.

Figure 2:
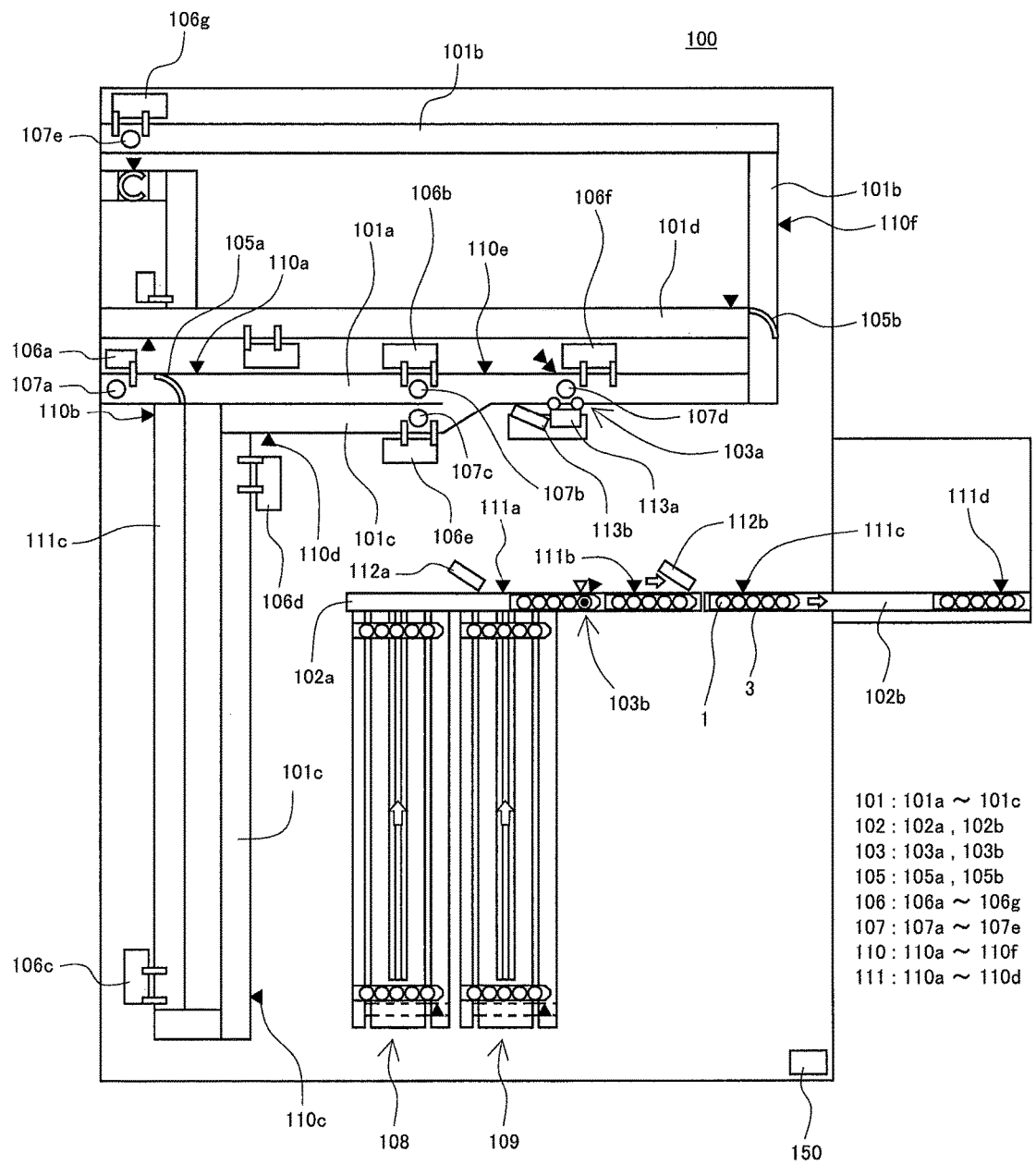
FIG. 2 is a diagram illustrating an entire configuration of a specimen container transfer mechanism part.

FIG. 2 is a diagram illustrating an entire configuration of the specimen container transfer mechanism part.

As mentioned above, the specimen container transfer mechanism parts 100, 200 transfer the specimen container 1 between the specimen container holder 2 capable of mounting the one specimen container 1 used in the preprocessing device 300 and the conveyance path 600 and the specimen container rack 3 capable of mounting the five specimen containers 5 used in the analysis devices 400, 500. Here, the specimen container transfer mechanism part 100 will be described on behalf of the plurality of specimen container transfer mechanism parts.

In FIG. 2, the specimen container transfer mechanism part 100 includes internal conveyance paths 101 (101a, 101b, 101c) which convey the specimen container holder 2 conveyed by the conveyance path 600 inside the specimen container transfer mechanism part 100, internal conveyance paths 102 (102a, 102b) which convey the specimen container rack 3 used in the analysis device 300 inside the specimen container transfer mechanism part 100, and a temporary stop switch 150 which temporarily stops supply of the specimen container rack 3 from the specimen container transfer mechanism part 100 to the analysis device 400.

The internal conveyance paths 101, 102 have configurations similar to the conveyance path 600. In other words, the internal conveyance paths 101, 102 are, for example, formed of belt conveyers driven by a rotary driving device (not illustrated). Even in a state in which the plurality of specimen container holders 2 is disposed on the belt conveyors, the internal conveyance paths 101, 102 can simultaneously convey the specimen container holders 2.

The internal conveyance path 101 and the internal conveyance path 102 are respectively provided with specimen container transfer positions 103 where transfer of the specimen container 1 is performed between the specimen container holder 2 and the specimen container rack 3 by a specimen container moving mechanism 104 described below (see FIGS. 5 to 12). The specimen container 1 is extracted from the specimen container holder 2 at the specimen container transfer position 103a on the internal conveyance path 101 side. Further, the specimen container 1 is mounted on the specimen container rack 3 at the specimen container transfer position 103b on the internal conveyance path 102 side.

The internal conveyance path 101 includes the internal conveyance path (a first internal conveyance path) 101a, the internal conveyance path (a third internal conveyance path) 101c, and the internal conveyance path (a second internal conveyance path) 101b. The internal conveyance path 101a conveys the specimen container holder 2 conveyed to the specimen container transfer mechanism part 100 by the conveyance path 600 to the specimen container transfer position 103a. The internal conveyance path 101c conveys the specimen container holder 2 conveyed to the specimen container transfer mechanism part 100 by the conveyance path 600 to the specimen container transfer position 103a via a distance at least longer than the internal conveyance path 101a. The internal conveyance path 101b conveys the specimen container holder 2 from the specimen container transfer position 103a to the conveyance path 600.

The internal conveyance path 101 is provided with internal conveyance path selection mechanisms 105a and 105b. The internal conveyance path selection mechanism 105a selectively switches the internal conveyance path 101 which conveys the specimen container holder 2 to the specimen container transfer position 103a between the internal conveyance path (the first conveyance path) 101a and the internal conveyance path (the third conveyance path) 101c. The internal conveyance path selection mechanism 105b controls the unnecessary holder so as not to be stagnated by switching the specimen container holder 2 emptied after completing transfer of the specimen container 1 at the specimen container transfer part 103 to retreat to a retreat conveyance path 101d.

Further, the internal conveyance path 101 is provided with a stopper mechanism 106 which temporarily stops, on the internal conveyance path 101, the specimen container holder 2 conveyed on the internal conveyance path 101.

The stopper mechanism 106 includes stopper mechanisms 106a to 106g. The stopper mechanism 106a stops the specimen container holder 2 conveyed to the specimen container transfer mechanism part 100 by the conveyance path 600 before entering the internal conveyance paths 101a, 101c. The stopper mechanism 106b stops the specimen container holder 2 conveyed on the internal conveyance path 101a before entering the specimen container transfer position 103a. The stopper mechanism 106c stops the specimen container holder 2 conveyed on the internal conveyance path 101c on an upstream side of the internal conveyance path 101c, and the stopper mechanism 106d stops the specimen container holder 2 on a downstream side thereof. The stopper mechanism 106e stops the specimen container holder 2 conveyed on the internal conveyance path 101c before entering the specimen container transfer position 103a. The stopper mechanism 106f stops the specimen container holder 2 conveyed on the internal conveyance path 101a or the internal conveyance path 101c at the specimen container transfer position 103a. The stopper mechanism 106g stops the specimen container holder 2 conveyed on the internal conveyance path 101b before entering the conveyance path 600.

Even in a case where the plurality of specimen container holders 2 is continuously conveyed on the conveyance line 101 and stagnates, the stopper mechanisms 106b to 106g have a function capable of separating the specimen container holders 2 one by one and conveying them to a downstream side of the internal conveyance path 101.

The specimen container transfer position 103a of the internal conveyance path 101 is provided with a rotation mechanism 113a and the bar code reader 113b. The rotation mechanism 113a laterally rotates the specimen container holder 2 stopped by the stopper mechanism 106f. The bar code reader 113b reads the bar code 1a of the specimen container 1 mounted on the specimen container holder 2 rotated by the rotation mechanism 113a and transmits it to the transfer control part 10a.

Further, the internal conveyance path 101 is provided with the RFID reader 107 which reads the RFID element 2a of the specimen container holder 2 conveyed on the internal conveyance path 101 and transmits information thereof to the transfer control part 10a.

The RFID reader 107 includes RFID readers 107a, 107b, 107c, 107d, and 107g. The RFID reader 107a reads the information of the RFID element 2a at a position of the stopper mechanism 106a where the specimen container holder 2 conveyed to the specimen container transfer mechanism part 100 by the conveyance path 600 is stopped before entering the internal conveyance paths 101a, 101c. The RFID reader 107b reads the information of the RFID element 2a at a position of the stopper mechanism 106b where the specimen container holder 2 conveyed on the internal conveyance path 101a is stopped before entering the specimen container transfer position 103a. The RFID reader 107c reads the information of the RFID element 2a at a position of the stopper mechanism 106e where the specimen container holder 2 conveyed on the internal conveyance path 101c is stopped before entering the specimen container transfer position 103a. The RFID reader 107d reads the information of the RFID element 2a at a position of the stopper mechanism 106f (i.e., the specimen container transfer position 103a) where the specimen container holder 2 conveyed on the internal conveyance path 101a or the internal conveyance path 101c is stopped at the specimen container transfer position 103a. The RFID reader 107g reads the information of the RFID element 2a at a position of the stopper mechanism 106g where the specimen container holder 2 conveyed on the internal conveyance path 101b is stopped before entering the conveyance path 600.

Further, the internal conveyance path 101 is provided with a holder detector 110 which detects passage of the specimen container holder 2 and transmits a detection result to the transfer control part 10a.

The holder detector 110 includes holder detectors 110a to 110f. The holder detector 110a detects that the specimen container holder 2 conveyed to the specimen container transfer mechanism part 100 by the conveyance path 600 has entered the internal conveyance path 101a. The holder detector 110b detects that the specimen container holder 2 conveyed to the specimen container transfer mechanism part 100 by the conveyance path 600 has entered the internal conveyance path 101c. The holder detector 110c detects that the specimen container holder 2 has passed through an intermediate point of the internal conveyance path 101c. The holder detector 110d detects that the specimen container holder 2 has arrived at the downstream side of the internal conveyance path 101c. The holder detector 110e detects that the specimen container holder 2 has entered the specimen container transfer position 103a. The holder detector 110f detects that the specimen container holder 2 has been carried out from the specimen container transfer position 103a and passed through the internal conveyance path 101b.

The internal conveyance path (a fourth internal conveyance path) 102 includes the internal conveyance paths 102a and 102b. The internal conveyance paths 102a on an upstream side conveys the specimen container rack 3 mounted with the specimen containers 1 to the specimen container transfer position 103b. The internal conveyance path 102b on a downstream side conveys the specimen container rack 3 carried out from the specimen container transfer position 103b to the downstream side to a conveyance path 300a of the analysis device 400. Since the internal conveyance path 102a and the internal conveyance path 102b are individually driven, the conveyance of the specimen container rack 3 to the specimen container transfer position 103b and the carrying-out thereof from the specimen container transfer position 103b to the downstream side by the internal conveyance path 102a can be performed separately from the conveyance of the specimen container rack 3 to the analysis device 400 by the internal conveyance path 102b.

Rack holding lanes 108, 109 for holding the plurality of specimen container racks 3 where no specimen container 1 is mounted are disposed on the upstream side of the internal conveyance path 102a. The plurality of specimen container racks 3 held by the rack holding lanes 108, 109 is successively carried out to the internal conveyance path 102a based on control of the transfer control part 10a.

Further, the internal conveyance path 102 is provided with a rack detector 111 which detects passage of the specimen container rack 3 and transmits a detection result to the transfer control part 10a.

The rack detector 111 includes rack detectors 111a to 111d. The rack detector 111a detects that the specimen container rack 3 carried out from the rack holding lanes 108, 109 to the internal conveyance path 102 has entered the specimen container transfer position 103b. The rack detector 111b detects that the specimen container rack 3 has been carried out from the specimen container transfer position 103b. The rack detector 111c detects that the specimen container rack 3 has entered the internal conveyance path 102b. The rack detector 111d detects that the specimen container rack 3 has been carried into the analysis device 400 from the internal conveyance path 102b.

Further, the internal conveyance path 102 is provided with the bar code reader 112 which reads the bar code 3a attached to the specimen container rack 3 and transmits it to the transfer control part 10a.

The bar code reader 112 includes a bar code reader 112a which reads the bar code 3a of the specimen container rack 3 disposed at the specimen container transfer position 103a and a bar code reader 112b which reads the bar code 3a of the specimen container rack 3 entered from the internal conveyance path 102a to the internal conveyance path 102b.

Here, the specimen container moving mechanism 104 which transfers the specimen container 1 from the specimen container holder 2 to the specimen container rack 3 at the specimen container transfer position 103 will be described with reference to FIGS. 5 to 12.

FIGS. 5 to 12 are diagrams each illustrating a state in which the specimen container is transferred by the specimen container moving mechanism. FIGS. 5 to 8 are diagrams each illustrating a state of extracting the specimen container from the specimen container holder. FIGS. 9 to 12 are diagrams each illustrating a state of mounting the specimen container on the specimen container rack.

Figure 5:
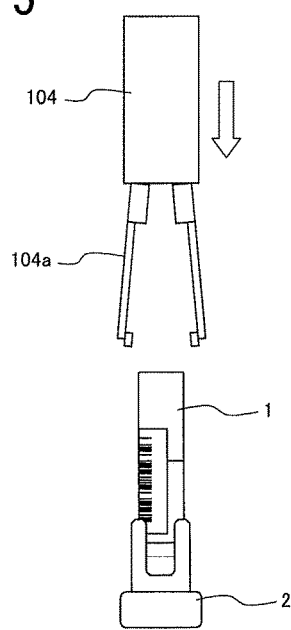
FIG. 5 is a diagram illustrating a state of extracting the specimen container from the specimen container holder.
Figure 6:
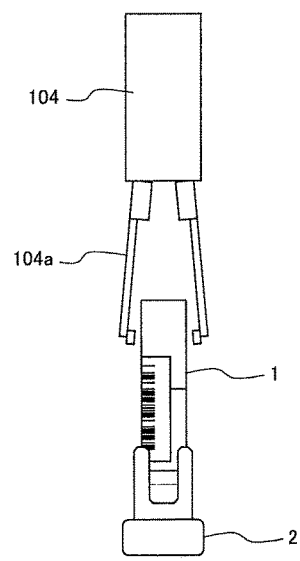
FIG. 6 is a diagram illustrating a state of extracting the specimen container from the specimen container holder.
Figure 7:
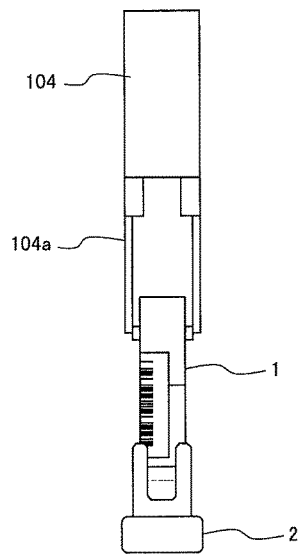
FIG. 7 is a diagram illustrating a state of extracting the specimen container from the specimen container holder.
Figure 8:
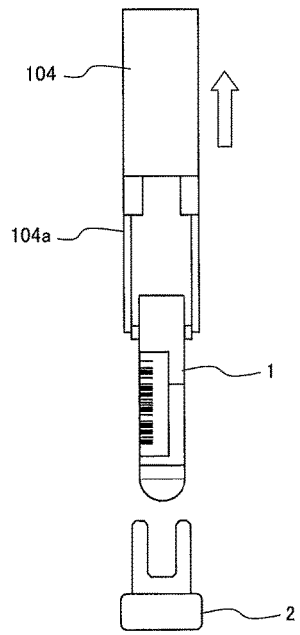
FIG. 8 is a diagram illustrating a state of extracting the specimen container from the specimen container holder.

At the specimen container transfer position 103a on the internal conveyance path 101 side, first, the specimen container moving mechanism 104 driven by a drive device (not illustrated) is moved to above the specimen container holder mounted with the specimen container 1 (see FIG. 5). Subsequently, the specimen container moving mechanism 104 is lowered close to the specimen container 1 (see FIG. 6). In this state, the specimen container 1 is gripped by a chuck mechanism 104a provided in the specimen container moving mechanism 104 (see FIG. 7). By moving the specimen container moving mechanism 104 upward as it is, the specimen container 1 is extracted from the specimen container holder 2 (FIG. 8).

Figure 9:
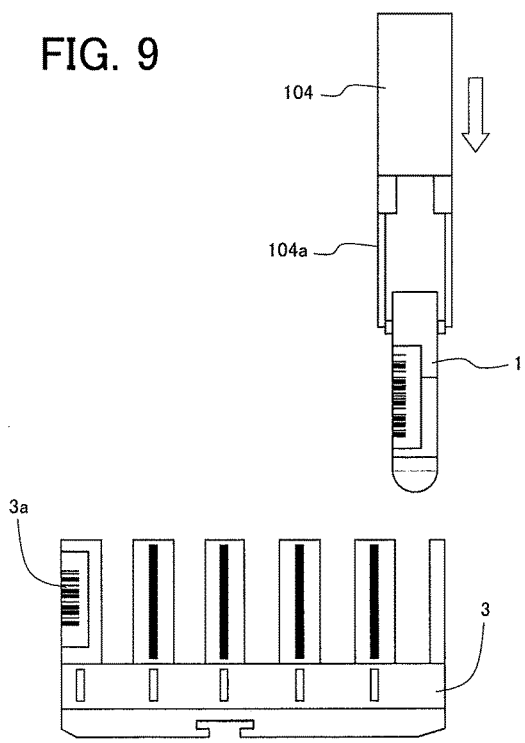
FIG. 9 is a diagram illustrating a state of mounting the specimen container on the specimen container rack.
Figure 10:
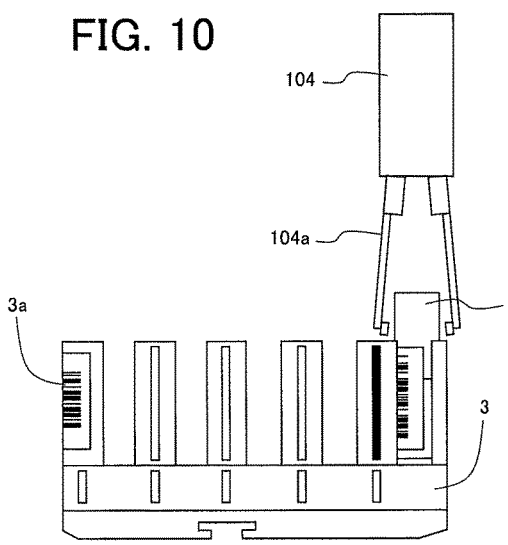
FIG. 10 is a diagram illustrating a state of mounting the specimen container on the specimen container rack.
Figure 11:
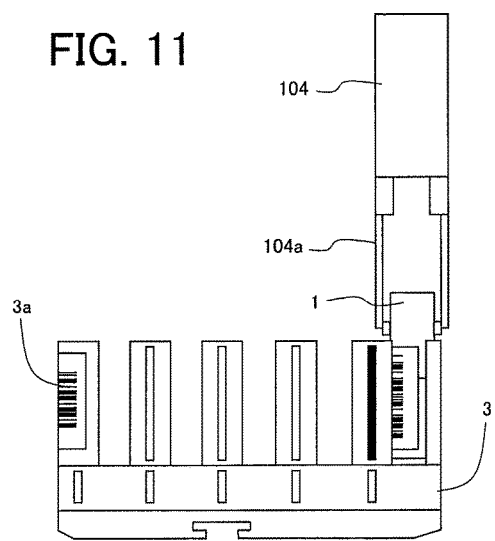
FIG. 11 is a diagram illustrating a state of mounting the specimen container on the specimen container rack.
Figure 12:
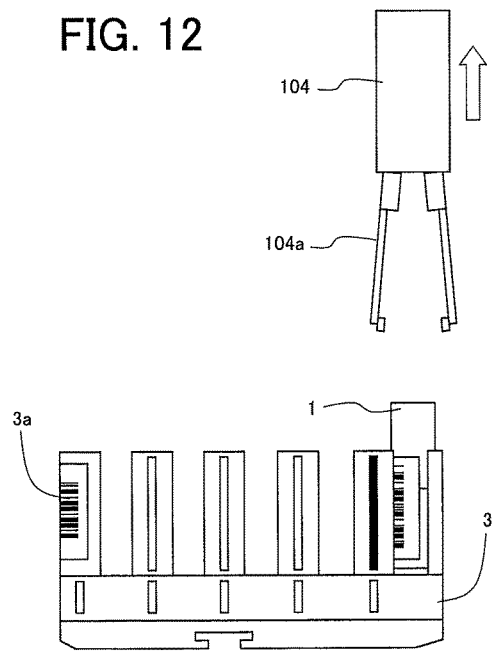
FIG. 12 is a diagram illustrating a state of mounting the specimen container on the specimen container rack.
Figure 13:
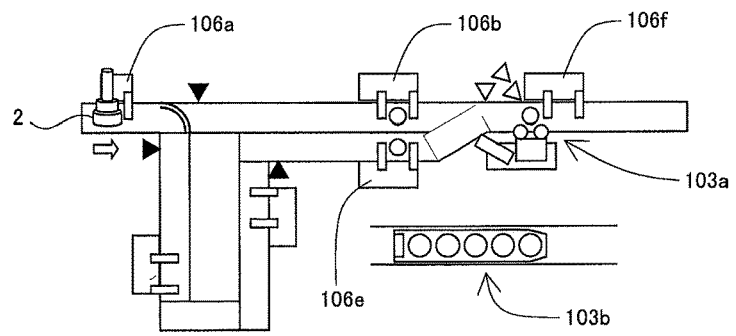
FIG. 13 is a diagram extracting and schematically illustrating a peripheral configuration of internal conveyance paths and a specimen container transfer position.

Next, at the specimen container transfer position 103b on the internal conveyance path 102 side, first, the specimen container moving mechanism 104 which grips the specimen container 1 by the chuck mechanism 104a is moved to above a mounting position of the specimen container rack 3 for mounting the specimen container 1 where no specimen container 1 is mounted (see FIG. 9). Subsequently, the specimen container 1 lowered to a position mounted on the specimen container rack 3 (see FIG. 10). In this state, the specimen container 1 is released by opening the chuck mechanism 104a of the specimen container moving mechanism 104 (see FIG. 11). By moving the specimen container moving mechanism 104 upward as it is, the specimen container 1 is mounted on the specimen container rack 3 (FIG. 12).

Next, priority order control in the internal conveyance path 101 of the specimen container transfer transfer mechanism part 100 will be described.

FIGS. 13 to 18 are diagrams each extracting and schematically illustrating a peripheral configuration of first, third, and fourth internal conveyance paths and the specimen container transfer position 103 of the specimen container transfer part.

In the present embodiment, the priority order control is control in which the specimen container 1 having relatively high priority order is preferentially conveyed to the analysis device 400 with respect to the other specimen, such as a general specimen, in a case where it is set to perform the analysis preferentially on the specimen container 1 thrown into the specimen processing system, that is, in a case where priority order of analysis is set high as with an urgent specimen.

In the priority order control, first, the specimen container holder 2 conveyed to the specimen container transfer mechanism part 100 by the conveyance path 600 is temporarily stopped by the stopper mechanism 106a. The RFID element 2a included in the specimen container holder 2 is read by the RFID reader 107a and is delayed to the transfer control part 10a (see FIG. 13).

The transfer control part 10a refers to information associated with identification information of the specimen stored in the storage part 10b of the control part 10 and setting of the priority order, reads the setting of the priority order of the specimen container 1, and then determines priority.

Figure 14:
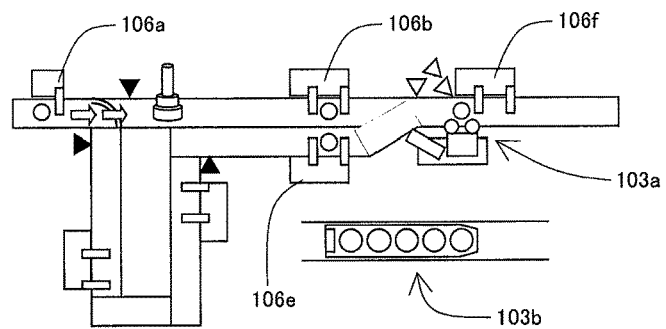
FIG. 14 is a diagram extracting and illustrating the internal conveyance paths and the specimen container transfer position.

When it is determined that the priority of analysis of the specimen container 1 is high in a determination result, the internal conveyance path selection mechanism 105a is controlled so that the corresponding specimen container holder 2 enters the internal conveyance path 101a, and the stopper mechanism 106a is opened (see FIG. 14). At this time, the specimen container holder 2 is conveyed to the internal conveyance path 101a and is temporarily stopped at the position of the stopper mechanism 106b (see FIG. 16).

Figure 15:
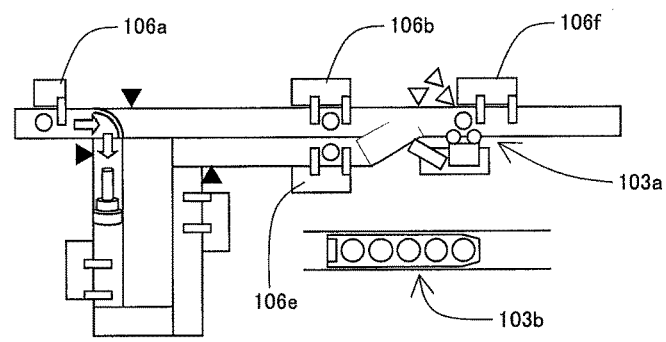
FIG. 15 is a diagram extracting and illustrating the internal conveyance paths and the specimen container transfer position.
Figure 16:
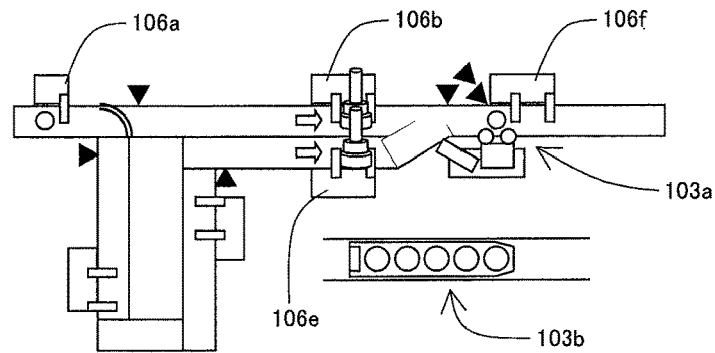
FIG. 16 is a diagram extracting and illustrating the internal conveyance paths and the specimen container transfer position.
Figure 17:
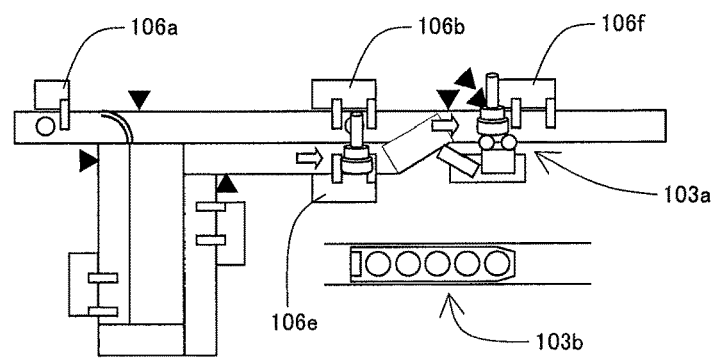
FIG. 17 is a diagram extracting and illustrating the internal conveyance paths and the specimen container transfer position.

Meanwhile, when it is determined that the priority of analysis of the specimen container 1 is low in the determination result, the internal conveyance path selection mechanism 105a is controlled so that the corresponding specimen container holder 2 enters the internal conveyance path (the third internal conveyance path) 101c which conveys the specimen container holder 2 to the specimen container transfer position 103a via a distance at least longer than the internal conveyance path 101a, and the stopper mechanism 106a is opened (see FIG. 15). At this time, the specimen container holder 2 is conveyed to the internal conveyance path 101c and is temporarily stopped at the position of the stopper mechanism 106e (see FIG. 16).

At this time, the specimen container holder 2 conveyed to the internal conveyance path 101a and stopped by the stopper mechanism 101b (i.e., the specimen container holder 2 mounted with the specimen container 1 which is determined that the priority of analysis is high) is preferentially opened with respect to the specimen container holder 2 conveyed to the internal conveyance path 101c and stopped by the stopper mechanism 101e (that is, the specimen container holder 2 mounted with the specimen container 1 which is determined that the priority of analysis is relatively low). The specimen container holder 2 is conveyed to the specimen container transfer position 103a (see FIG. 17).

Figure 18:
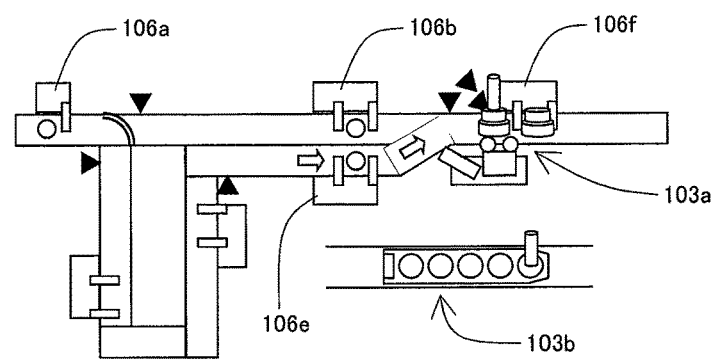
FIG. 18 is a diagram extracting and illustrating the internal conveyance paths and the specimen container transfer position.

Further, in a case where the specimen container holder 2 mounted with the specimen container 1 having high priority does not exist on the internal conveyance path 101a side, the specimen container holder 2 stopped by the stopper mechanism 101e is released and conveyed to the specimen container transfer position 103a (see FIG. 18).

It should be noted that the stopper mechanism 106f is controlled so as not to retain the specimen container holders 2 at the specimen container transfer position 103a more than necessary, and is controlled so as to sequentially extract the specimen container holders 2 stopped at the stopper mechanism 106b or the stopper mechanism 106f as soon as the transfer of the specimen container 1 at the specimen container transfer position 103a is completed.

In this way, in the priority order control of the present embodiment, the specimen having high priority (e.g., the urgent specimen) can overtake the specimen having relatively low priority (e.g., the general specimen). Further, the internal conveyance path 101c in the present embodiment is configured so that the specimen container holder 2 is conveyed to the specimen container transfer position 103a via the distance at least longer than the internal conveyance path 101a. Accordingly, the internal conveyance path 101c has a buffer function capable of holding the multiple specimen container holders 2 mounted with the specimen containers 1 having relatively low priority. In this way, since the multiple specimen containers 1 can be held, the analysis processing can be performed on the specimen container 1 having high priority in preference to the multiple specimen containers 1.

Next, avoidance control in the internal conveyance path 101 of the specimen container transfer transfer mechanism part 100 will be described.

FIGS. 19 to 24 are diagrams each extracting and schematically illustrating a peripheral configuration of the first to third internal conveyance paths and the specimen container transfer position 103a of the specimen container transfer part.

In the present embodiment, the avoidance control is control in which the specimen container holder 2 already carried into the specimen container transfer mechanism part 100 is conveyed to the other specifiable analysis device (the analysis device 500 in the present embodiment) in a case where the analysis device 400 is brought into an unusable state.

Figure 19:
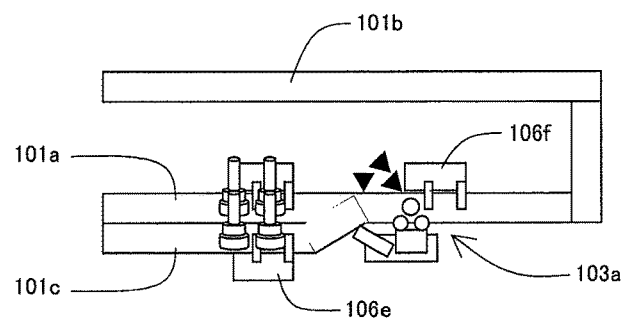
FIG. 19 is a diagram extracting and illustrating the internal conveyance paths and the specimen container transfer position.

In the avoidance control, in a case where the specimen container holders 2 exist in the internal conveyance paths 101a, 101c, when it is determined that the analysis device 400 is in the unusable state, the specimen container holders 2 are temporarily stopped by the stopper mechanisms 106b, 106e (see FIG. 19).

Figure 20:
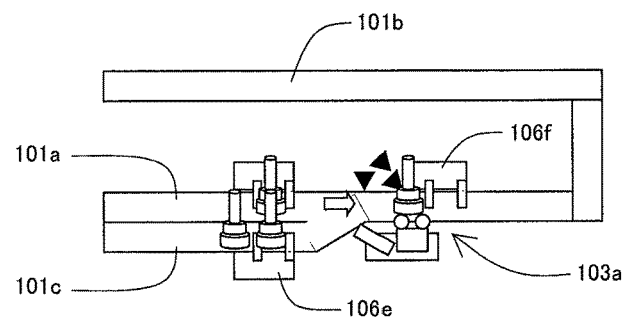
FIG. 20 is a diagram extracting and illustrating the internal conveyance paths and the specimen container transfer position.
Figure 21:
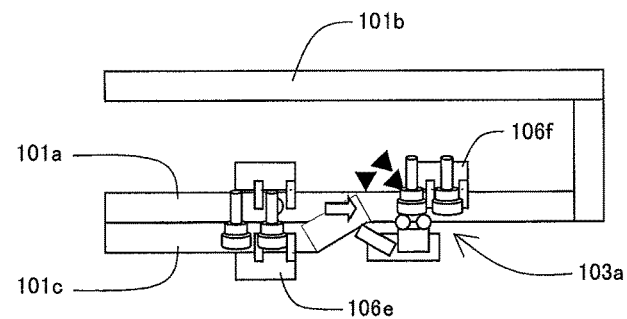
FIG. 21 is a diagram extracting and illustrating the internal conveyance paths and the specimen container transfer position.
Figure 22:
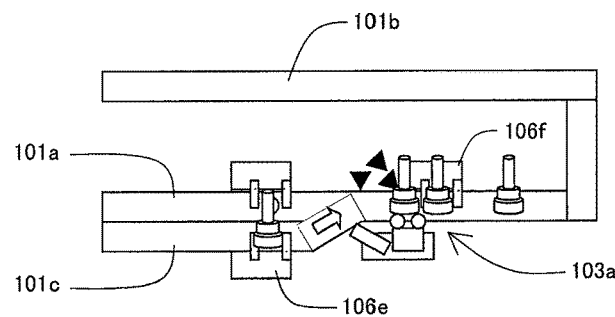
FIG. 22 is a diagram extracting and illustrating the internal conveyance paths and the specimen container transfer position.
Figure 23:
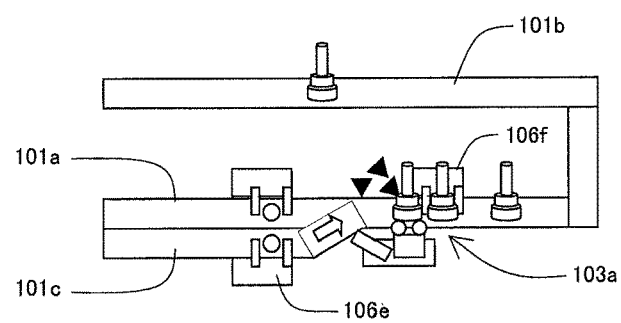
FIG. 23 is a diagram extracting and illustrating the internal conveyance paths and the specimen container transfer position.
Figure 24:
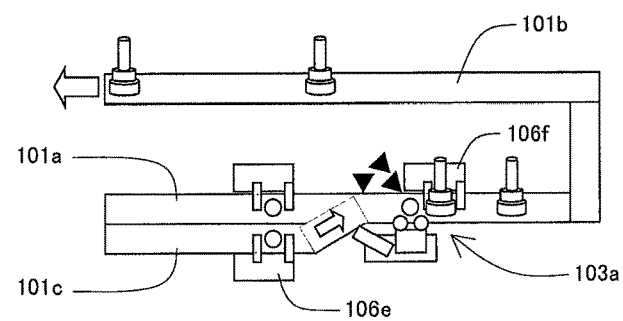
FIG. 24 is a diagram extracting and illustrating the internal conveyance paths and the specimen container transfer position.

Next, the stopper mechanisms 106b on the internal conveyance path 101a side is opened, and the stopped specimen container holder 2 is conveyed to the specimen container transfer position 103a side (see FIG. 20). When the specimen container holder 2 stopped on the internal conveyance path 101a side does not exist (see FIG. 21), the stopper mechanism 106e on the internal conveyance path 101c side is subsequently opened, and the stopped specimen container holder 2 is conveyed to the downstream side (see FIG. 22).

The specimen container holder 2 conveyed to the specimen container transfer position 103a is temporarily stopped by the stopper mechanism 106f. However, transfer of the specimen container 1 is not performed. The specimen container holder 2 is conveyed to the conveyance path 600 via the internal conveyance path 101b as it is and conveyed to the other analysis device (e.g., the analysis device 500) (see FIG. 23). In the case where the analysis device 400 is in the unusable state, this is performed on all of the specimen container holders 2 conveyed to the specimen container transfer mechanism part 100 (see FIG. 24).

As the state in which the analysis device 400 is unusable, a case of a temporary unusable state caused by a steady action, such as reagent replacement, and a case of a long unusable state caused by a mechanical failure can be considered. Restoration is easy in a case of the temporary unusable state as with the former case. Accordingly, the specimen container holder 2 may be controlled to wait without performing path avoidance. Further, in a case of the long unusable state as with the latter case, there is a possibility of taking time which includes time up to the restoration. The specimen container holder 2 conveyed to the specimen container transfer mechanism part 100 while the analysis device 400 is recognized to be in the unusable state is conveyed to the other analyzable analysis device 500 before transfer is performed. Accordingly, the number of transferred specimens can be suppressed as much as possible, and it is possible to minimize processing of restoration work after the device is unusable.

Next, a path determination control in the specimen processing system of the present embodiment will be described.

In the present embodiment, the path determination control is to shorten a processing time of the specimen 1b as the entire specimen processing system by controlling conveyance of the specimen container holder 2 so that loads of transfer of the plurality of specimen container transfer mechanism parts 100, 200 are dispersed as much as possible.

It should be noted that, when the specimen container holder 2 passes through a conveyance path conversion mechanism 600a of the conveyance path 600 disposed at a carrying-out part of the preprocessing device 300, it is determined that the specimen container holder 2 is conveyed to which of the specimen container transfer mechanism parts 100, 200.

Here, specimen processing system information used in the priority order control, the avoidance control, and the path determination control described above will be described.

Figure 25:
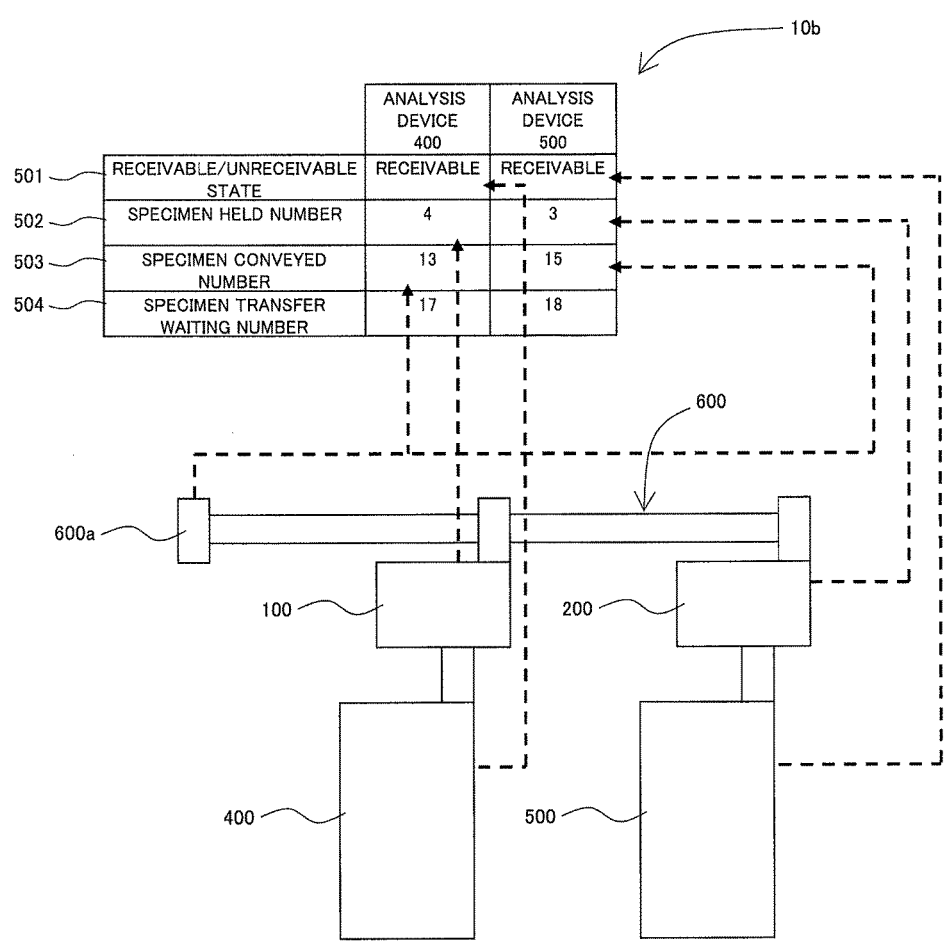
FIG. 25 is a diagram exemplarily illustrating a configuration of specimen processing system information.

FIG. 25 is a diagram exemplarily illustrating a configuration of the specimen processing system information in the storage part 10b and a flow of each information configuring the specimen processing system information.

In FIG. 25, the specimen processing system information has a state 501 in which specimens are receivable or not (hereinafter referred to as a specimen receivable/unreceivable state 501) in the analysis system 400, 500 reported from the specimen container transfer mechanism part 100, 200, a number 502 of specimens held (hereinafter referred to as a specimen held number 502) reported from the specimen transfer container mechanism part 100, 200, a number 503 of specimens conveyed (hereinafter referred to as a specimen conveyed number 503) at the time of instructing to the conveyance path conversion mechanism 600a, and a number 504 of specimens waiting for transfer (hereinafter referred to as a specimen transfer waiting number 504) which is the sum of the specimen held number 502 and the specimen conveyed number 503.

The control part 10 and the transfer control part 10b always monitor whether the analysis systems 400, 500 are in states capable of receiving the specimen container rack 3 from the specimen container transfer mechanism parts 100, 200. This information is transmitted to the control part 10 and the transfer control part 10b from the specimen container transfer mechanism parts 100, 200 and is registered in the receivable/unreceivable state information 501 for every analysis device.

Further, when the specimen container holder 2 conveyed by the conveyance path 600 arrives at the specimen container transfer mechanism part 100, 200, an arrival report of the specimen container holder 2 is reported to the control part 10 and the transfer control part 10b. Every time the control part 10 and the transfer control part 10b receive the arrival report, one is added to the specimen held number 502 and one is subtracted from the specimen conveyed number 503. Further, in a case where transfer of the specimen container 1 is performed, or in a case where performance of the transfer is determined to be unnecessary and the specimen container holder 2 passes through the specimen container transfer position 103a, one is subtracted from the specimen held number 502. In other words, the specimen held number 502 is the number of specimens which are held in the specimen container transfer mechanism parts 100, 200 and wait for the transfer from the holder to the rack, and the specimen conveyed number is a numerical value meaning the number of specimens in the conveyance path conversion mechanism 600a which are in the middle of being conveyed to the respective specimen container transfer mechanism parts 100, 200. The number obtained by adding up the specimen held number 502 and the specimen conveyed number 503 is the specimen transfer waiting number 504.

In other words, by referring to two information of the receivable/unreceivable state 501 and the specimen transfer waiting number 504, states and loads of the analysis systems 400, 500 connected to the specimen container transfer mechanism parts 100, 200 at that moment can be recognized. When the new specimen container holder 2 is conveyed, the control part 10 and the transfer control part 10b select the conveyance path by using the receivable/unreceivable state information 501 which is receivable and the information of the specimen transfer waiting number 504.

For example, in a case where the path to convey the specimen container 2 is only to the analysis system 400, it is determined whether the receivable/unreceivable state information 501 reported from the specimen container transfer mechanism part 100 is receivable. If it is receivable, the path which conveys to the specimen container transfer mechanism part 100 is selected.

Further, in a case where the path to convey the specimen container 2 can be the analysis system 400 or the analysis system 500, any of the specimen receivable/unreceivable state information 501 reported from the specimen container transfer mechanism parts 100, 200 which is receivable is selected.

Furthermore, in a case where the path to convey the specimen container 2 can be to the analysis system 400 or the analysis system 500 and any of the receivable/unreceivable state information 501 reported from the specimen container transfer mechanism parts 100, 200 is receivable, the time required by the specimen container 1 for arriving at the analysis system can be shortened by selecting the smaller specimen transfer waiting number 504.

Subsequently, the path determination control in the specimen processing system of the present embodiment will be further described in detail.

Figure 26:
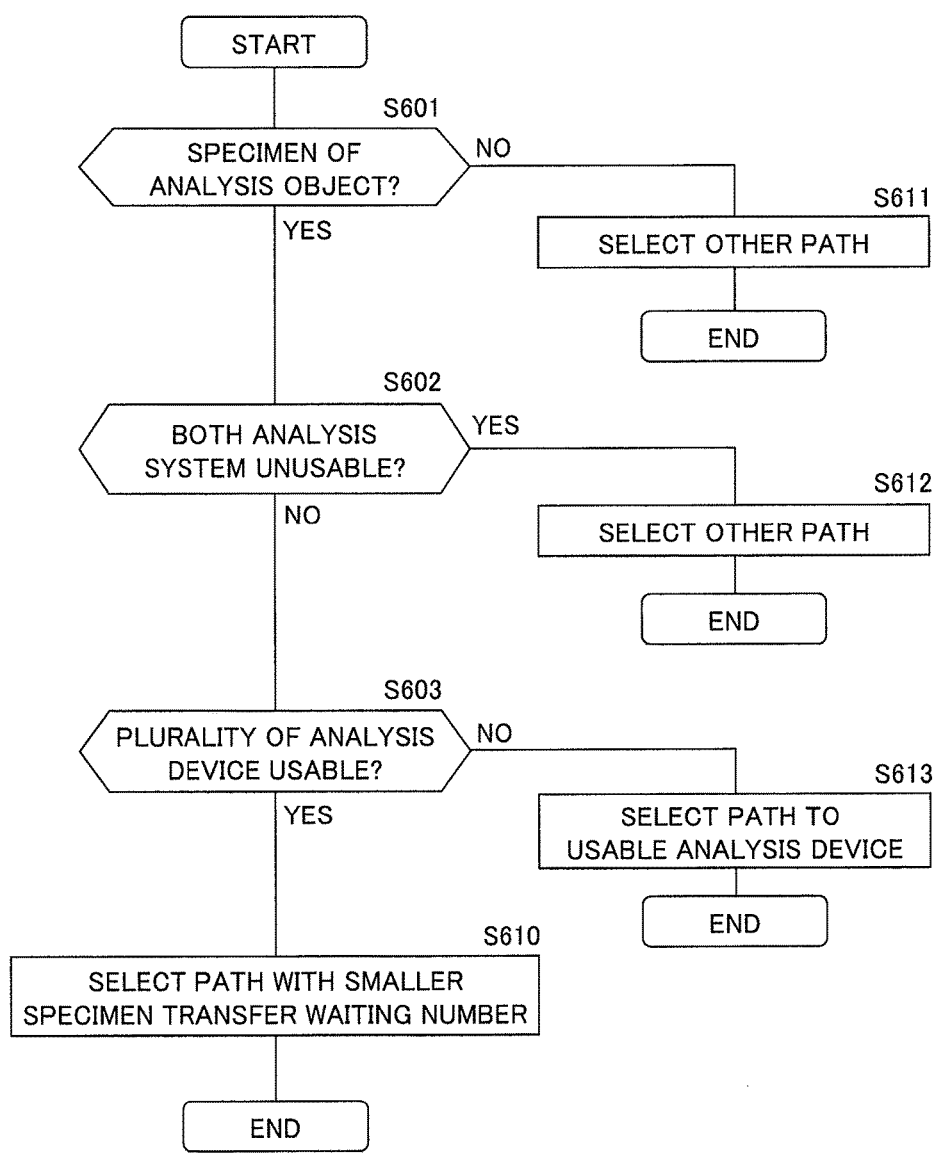
FIG. 26 is a flowchart illustrating details of conveyance path determination control.

FIG. 26 is a flowchart illustrating details of the conveyance path determination control.

In FIG. 26, the transfer control part 10b first determines whether the specimen container holder 2 has erroneously arrived at the conveyance path conversion mechanism 600a (step S601). If it is determined that the erroneous specimen has arrived, that is, if a determination result is NO, for example, another bypass for performing collection in a specimen collection module is selected (step S611), and then the processing is completed. Further, if the determination result in step S601 is YES, it is determined whether all of the analysis devices 400, 500 are in unusable states (step S602) (here, the determination is made by using the aforementioned receivable/unreceivable state information 501). If a determination result is YES, for example, the other bypass for performing collection in the specimen collection module is selected (step S612), and then the processing is completed. Further, if the determination result in step S602 is NO, it is determined whether the plurality of analysis devices 400, 500 are in usable states (step S603) (here, the determination is made by using the aforementioned receivable/unreceivable state information 501). If a determination result is NO, a path which conveys to the analysis device in the usable state is selected (step S613), and then the processing is completed. Further, if the determination result in step S603 is YES, the path having smaller specimen transfer waiting number (here, determination is made by using the aforementioned specimen transfer waiting number 504) is selected (step S610), and then the processing is completed.

Next, the avoidance control in the specimen processing system of the present embodiment will be further described in detail.

Figure 27:
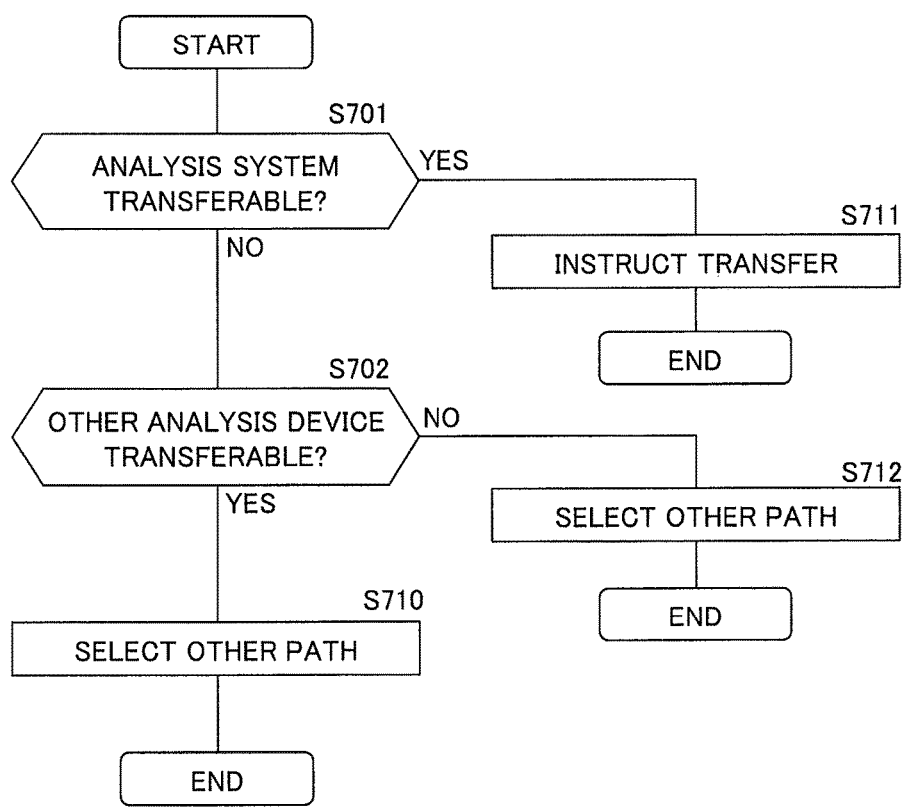
FIG. 27 is a flowchart illustrating details of avoidance control.

FIG. 27 is a flowchart illustrating details of the avoidance control.

In FIG. 27, when the conveyance container holder 2 has arrived, the transfer control part 10b first determines whether the analysis device 400, 500 connected to the specimen container transfer mechanism part 100, 200 is in a usable state (step S701). If a determination result is YES, transfer of the specimen container 1 in the specimen container transfer mechanism part 100, 200 is instructed (step S711), and then the processing is completed. Further, if the determination result in step S701 is NO, it is determined whether the other analysis device is in the usable state (step S702). If a determination result is YES, instruction is made to select the path which conveys again to the other analysis device in an analyzable state (step S710), and then the processing is completed. Further, if the determination result in step S702 is NO, instruction is made to wait in the specimen container transfer mechanism part 100, 200 or to convey to a predetermined position of a dedicated specimen collection module or the like to be analyzed by an analysis device other than the online analysis devices (step S712), and then the processing is completed.

Effects of the present embodiment configured as described above will be described.

There is a case where a kind/shape of a carrier which holds a specimen container containing a specimen is different among a preprocessing device, a plurality of analysis devices, and the like which configure a specimen processing system. Therefore, in such a case, it is necessary that the specimen container is transferred to the carrier corresponding to each analysis device by a transfer device provided at a portion connected with each of the plurality of analysis devices in a conveyance path for the specimen container.

However, in a conventional technology, in a case where replenishment of a reagent used for the specimen analysis is required or where the analysis device serving as a conveyance destination of the specimen container is brought into an unusable state by failure or the like, it is considered that the specimen container conveyed to the analysis device stagnates in the transfer device or on the conveyance path. Also, it is concerned that the analysis processing of each specimen is delayed or that throughput of the analysis processing in the entire specimen analysis system is reduced.

Meanwhile, in the present embodiment, it is configured to include the specimen container transfer mechanism part and the transfer control part. The specimen container transfer mechanism part is disposed between the conveyance path which conveys the first carrier mounted with the specimen container, in which the specimen is contained, to one of the plurality of conveyance destinations and the conveyance destination. The specimen container transfer mechanism part transfers the specimen container between the first carrier conveyed by the conveyance path and the second carrier used for mounting and conveying the specimen container at the conveyance destination. The transfer control part determines whether the conveyance destination is in the state suitable for receiving the specimen container. If it is determined that the conveyance destination is in the state unsuitable for reception, the transfer control part controls the specimen container transfer mechanism part so as to convey the first carrier to the other conveyance destination via the conveyance path. Accordingly, delay in the analysis processing or reduction in throughput can be suppressed.

Further, since the specimen to be conveyed is collected from a patient, there is a degree of urgency. There are naturally some specimens which must be given priority and other specimens which have no problem even if time elapses. Accordingly, the control in which some specimens are analyzed more preferentially than the other specimens is performed as urgent specimen processing in the analysis system. The same is also performed on the preprocessing device. In the present embodiment, since it is controlled that the specimen with high urgency is preferentially transferred and rapidly conveyed to the analysis device, the analysis result of the specimen with high urgency can be preferentially obtained.

A case of using the two analysis devices has been described as an example as a specimen processing system in the present embodiment. However, the present invention is not limited to this and can be similarly applied to a case of using three or more analysis devices.

<Second Embodiment>

A second embodiment of the present invention will be described with reference to FIGS. 28 to 33.

In the present embodiment, an internal conveyance path 102 of a specimen container transfer mechanism part 100 includes rack holding lanes 161, 162 which temporarily retain a specimen container rack 3 mounted with specimen containers 1.

Figure 28:
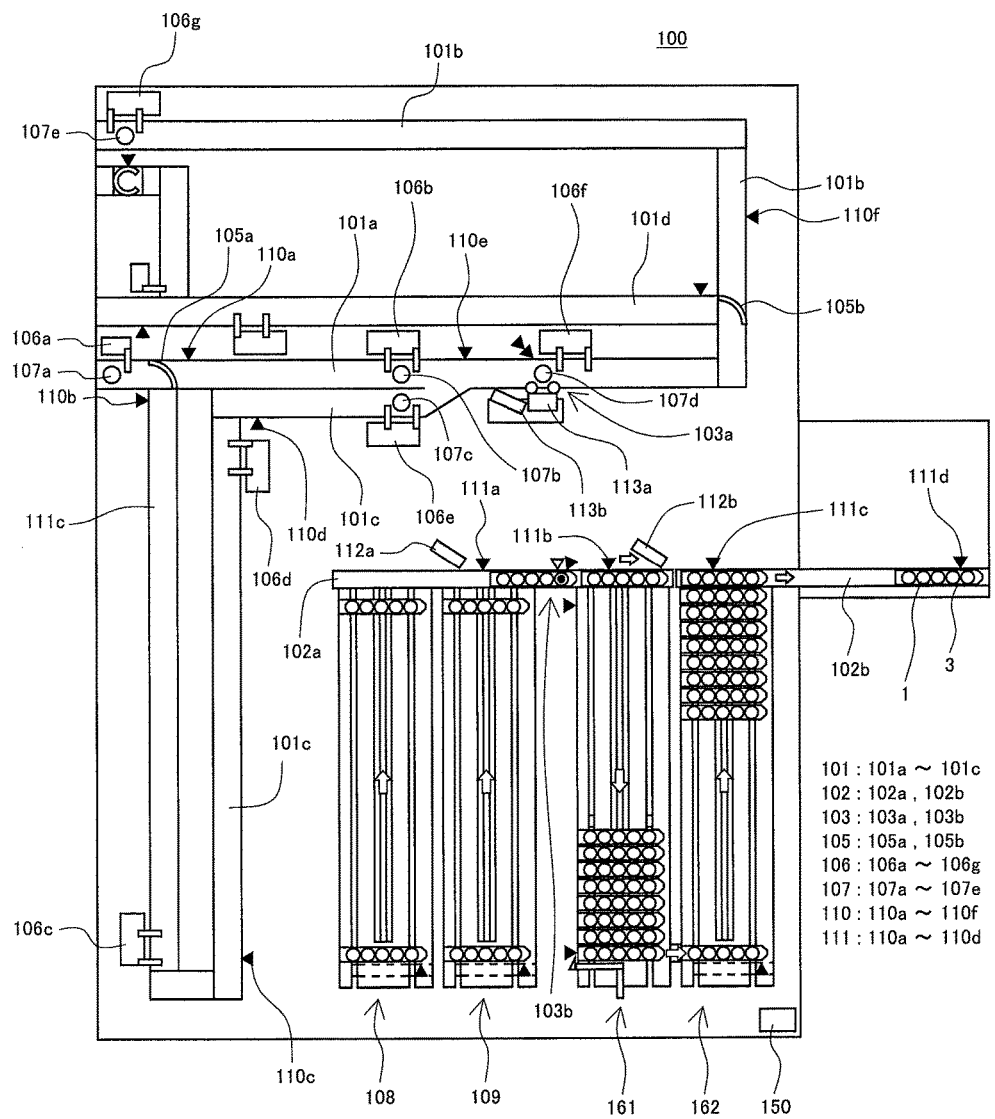
FIG. 28 is a diagram illustrating an entire configuration of a specimen container transfer mechanism part according to a second embodiment.
Figure 29:
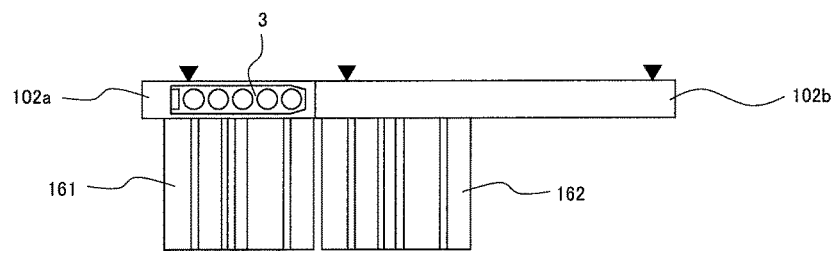
FIG. 29 is a diagram illustrating a state of a specimen container rack in rack holding lanes.
Figure 30:
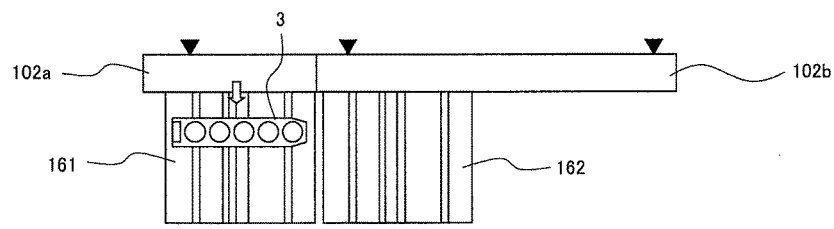
FIG. 30 is a diagram illustrating a state of the specimen container rack in the rack holding lanes.
Figure 31:
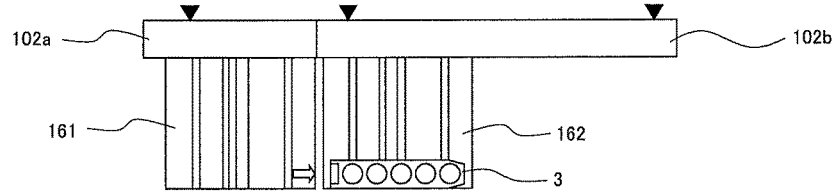
FIG. 31 is a diagram illustrating a state of the specimen container rack in the rack holding lanes.
Figure 32:
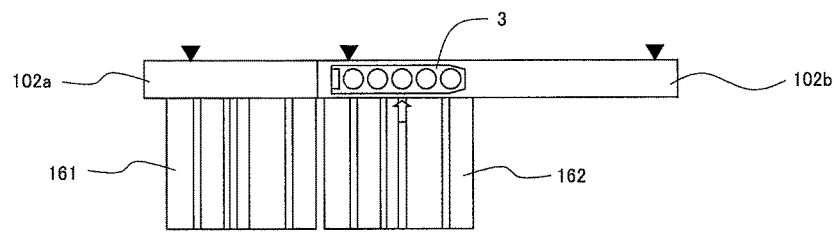
FIG. 32 is a diagram illustrating a state of the specimen container rack in the rack holding lanes.

FIG. 28 is a diagram illustrating an entire configuration of the specimen container transfer mechanism part according to the present embodiment, and FIGS. 29 to 33 are diagrams illustrating states in which the specimen container rack 3 is held by the rack holding lanes. Same reference signs are assigned to members identical to those in the first embodiment throughout the drawings, and descriptions thereof are omitted.

In FIG. 28, the rack holding lanes 161, 162 are disposed so as to step over a connection part between a downstream side end part of an internal conveyance path 102a and an upstream side end part of an internal conveyance path 102b.

The rack holding lanes 161, 162 have sequential buffer structures. When the specimen container rack 3 mounted with the specimen containers 1 has arrived at the downstream side end part of the internal conveyance path 102a (see FIG. 29), in a case where priority of the specimen container rack 3 mounted with the specimen containers 1 corresponds to a general specimen, the specimen container rack 3 is carried into the rack holding lane 161 (see FIG. 30). The specimen container rack 3 is conveyed to a downstream end part of the rack holding lane 161 and is moved to the rack holding lane 162 side (see FIG. 31). After that, the specimen container rack 3 is carried out from a downstream side end part of the rack holding lane 162 to the internal conveyance path 102b (see FIG. 32), and is conveyed to an analysis device 400 (see FIG. 33).

Figure 33:
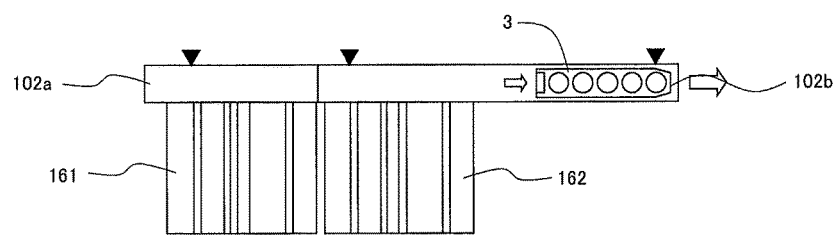
FIG. 33 is a diagram illustrating a state of the specimen container rack in the rack holding lanes.

Further, when the specimen container rack 3 mounted with the specimen containers 1 has arrived at the downstream side end part of the internal conveyance path 102a (see FIG. 29), in a case where priority of the specimen container rack 3 mounted with the specimen containers 1 corresponds to an urgent specimen, the specimen container rack 3 is carried out to the internal conveyance path 102b without passing through the rack holding lanes 161, 162 (see FIG. 32), and is conveyed to the analysis device 400 (see FIG. 33).

Other configurations are similar to those in the first embodiment.

Effects similar to those in the first embodiment can be obtained in the present embodiment configured as described above.

Further, in a case of the specimen container rack 3 including the specimen with urgent priority, it is possible to overtake the general specimen and supply the specimen container rack 3 to the analysis device 400.

<Third Embodiment>

A third embodiment of the present invention will be described with reference to FIGS. 34 to 42.

In the present embodiment, an internal conveyance path 102 of a specimen container transfer mechanism part 100 includes rack holding lanes 163, 164 which temporarily retain a specimen container rack 3 mounted with specimen containers 1.

Figure 34:
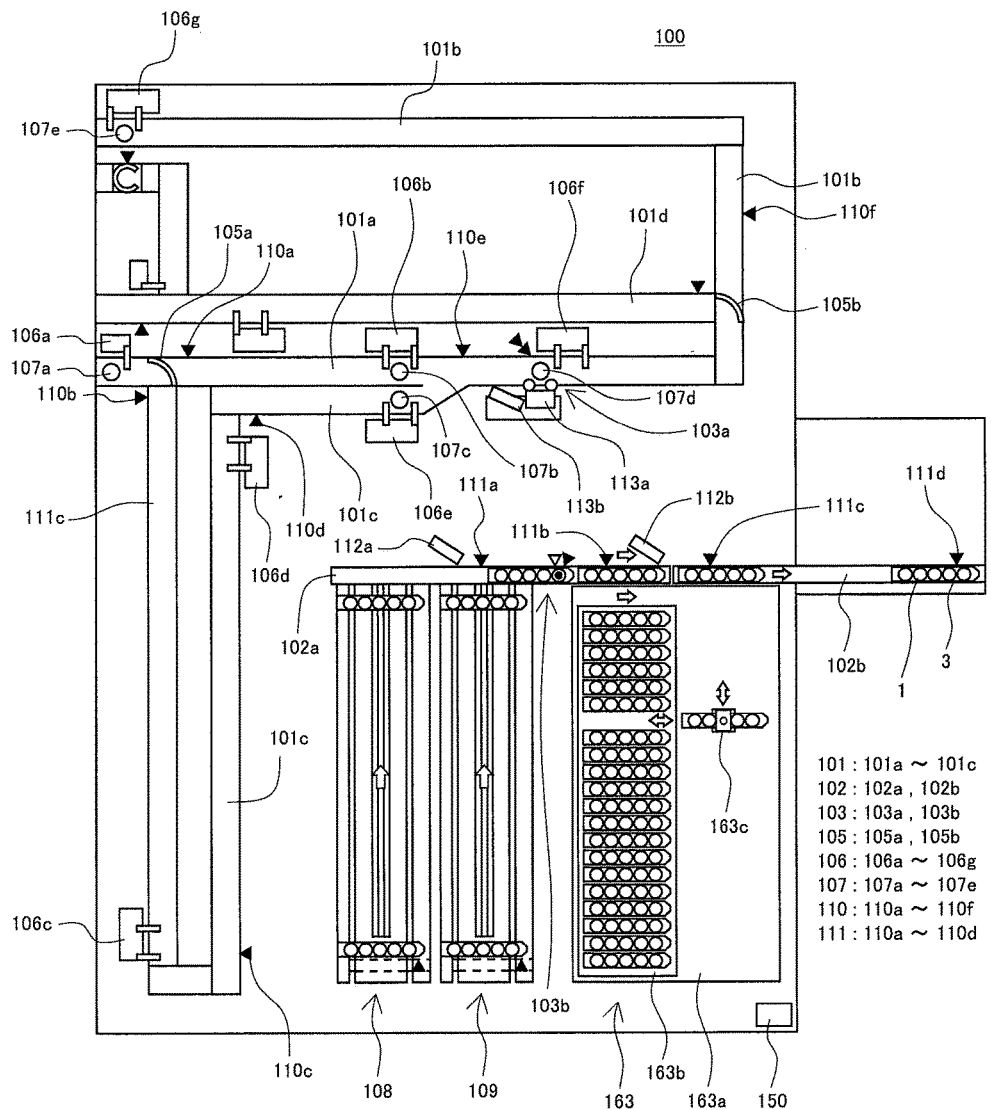
FIG. 34 is a diagram illustrating an entire configuration of a specimen container transfer mechanism part according to a third embodiment.
Figure 35:
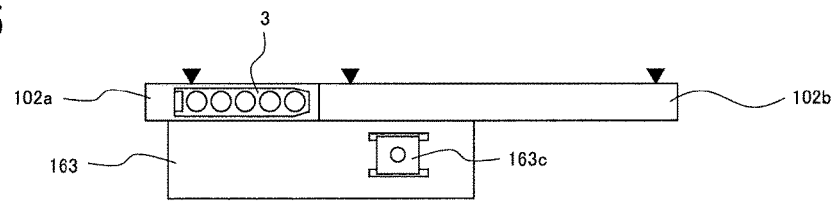
FIG. 35 is a diagram illustrating a state of a specimen container rack in a rack holding lane.
Figure 36:
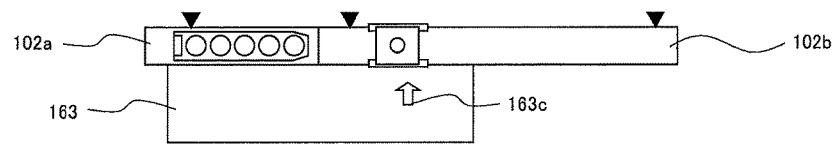
FIG. 36 is a diagram illustrating a state of the specimen container rack in the rack holding lane.
Figure 37:
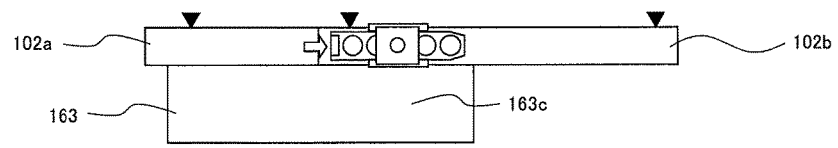
FIG. 37 is a diagram illustrating a state of the specimen container rack in the rack holding lane.
Figure 38:
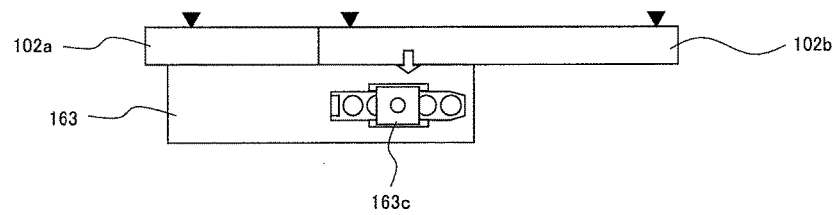
FIG. 38 is a diagram illustrating a state of the specimen container rack in the rack holding lane.
Figure 39:
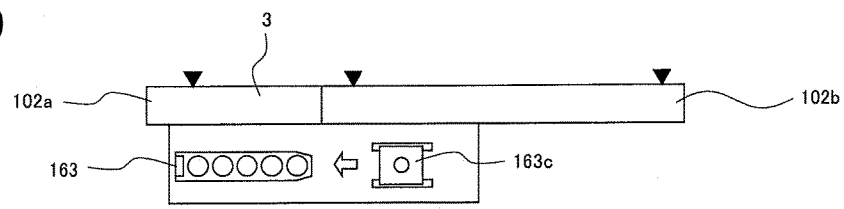
FIG. 39 is a diagram illustrating a state of the specimen container rack in the rack holding lane.
Figure 40:
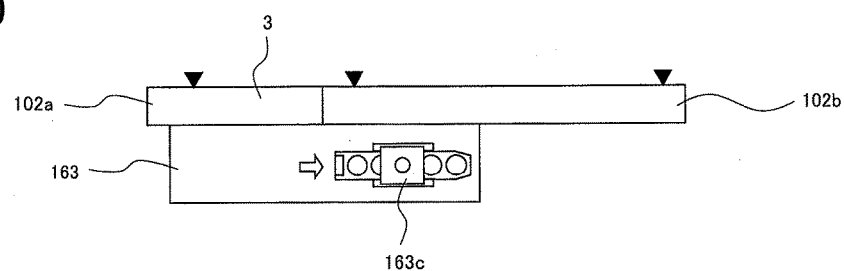
FIG. 40 is a diagram illustrating a state of the specimen container rack in the rack holding lane.
Figure 41:
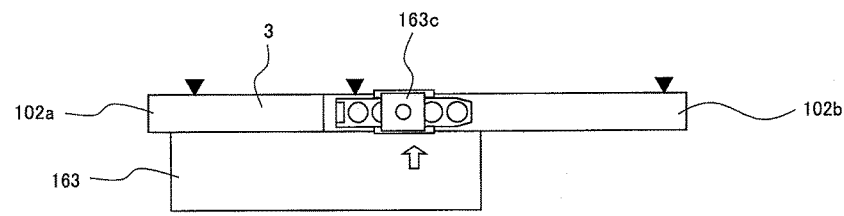
FIG. 41 is a diagram illustrating a state of the specimen container rack in the rack holding lane.

FIG. 34 is a diagram illustrating an entire configuration of the specimen container transfer mechanism part according to the present embodiment, and FIGS. 35 to 42 are diagrams illustrating states in which the specimen container rack 3 is held by the rack holding lane. Same reference signs are assigned to members identical to those in the first embodiment throughout the drawings, and descriptions thereof are omitted.

In FIG. 34, the rack holding lane 163 is disposed so as to step over a connection part between a downstream side end part of an internal conveyance path 102a and an upstream side end part of an internal conveyance path 102b.

The rack holding lane 163 has a random access buffer structure. When the specimen container rack 3 mounted with the specimen containers 1 has arrived at the upstream side end part of the internal conveyance path 102b via the downstream side end part of the internal conveyance path 102a (see FIGS. 35, 36), in a case where priority of the specimen container rack 3 mounted with the specimen containers 1 corresponds to a general specimen, the specimen container rack 3 is carried into a stock area 163b via a work area 163a of the rack holding lane 163 by a moving arm 163c (see FIGS. 37 to 39). The specimen container rack 3 to be conveyed to an analysis device 400 is moved from the stock area 163b by the moving arm 163c in the work area 163a (see FIG. 40). The specimen container rack 3 is carried out to the internal conveyance path 102b (see FIG. 41), and is conveyed to the analysis device 400 (see FIG. 42).

Figure 42:
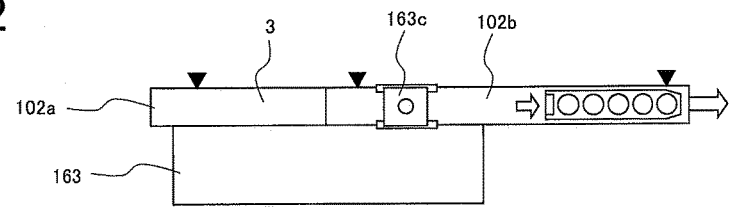
FIG. 42 is a diagram illustrating a state of the specimen container rack in the rack holding lane.

Further, when the specimen container rack 3 mounted with the specimen containers 1 has arrived at the upstream side end part of the internal conveyance path 102b via the downstream side end part of the internal conveyance path 102a (see FIG. 35), in a case where priority of the specimen container rack 3 mounted with the specimen containers 1 corresponds to an urgent specimen, the specimen container rack 3 is conveyed to the analysis device 400 by the internal conveyance path 102b without passing through the rack holding lane 163 (see FIG. 42).

Other configurations are similar to those in the first embodiment.

Effects similar to those in the first embodiment can be obtained in the present embodiment configured as described above.

Further, in a case of the specimen container rack 3 including the specimen with urgent priority, it is possible to overtake the general specimen and supply the specimen container rack 3 to the analysis device 400.

Further, accordingly, even in a case where the urgent specimens are continuous, it is possible to minimize an influence on the transfer act and is possible to control the priority of analysis.

<Fourth Embodiment>

A fourth embodiment of the present invention will be described with reference to FIGS. 43 to 48.

In the present embodiment, an internal conveyance path 102 of a specimen container transfer mechanism part 100 includes a conveyance path 102c which conveys a specimen container rack 3 from an analysis device 400 to the specimen container transfer mechanism part 100, and an internal conveyance path 101b includes a stopper mechanism 106h which temporarily stops an empty specimen container holder 2.

Figure 43:
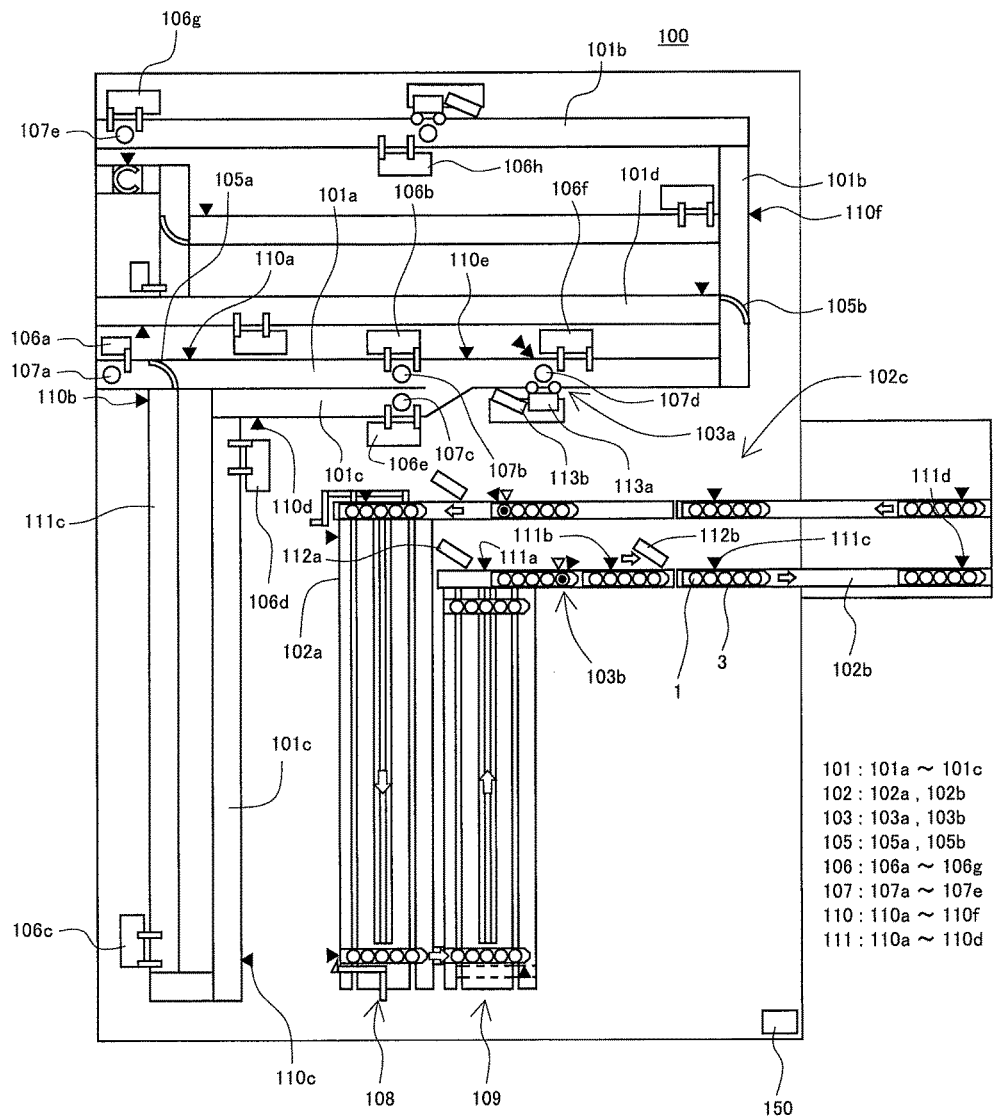
FIG. 43 is a diagram illustrating an entire configuration of a specimen container transfer mechanism part according to a fourth embodiment.
Figure 44:
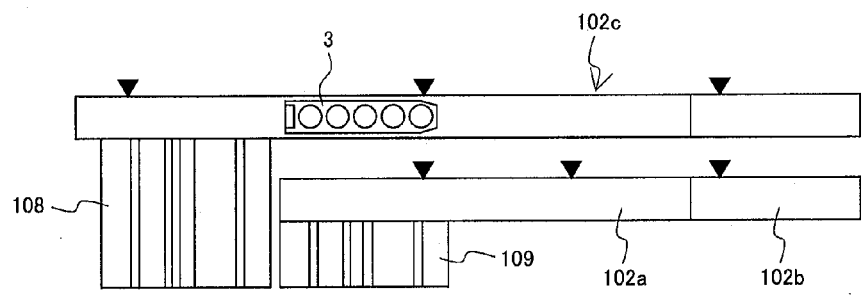
FIG. 44 is a diagram illustrating a state of a specimen container rack in internal conveyance paths.
Figure 45:
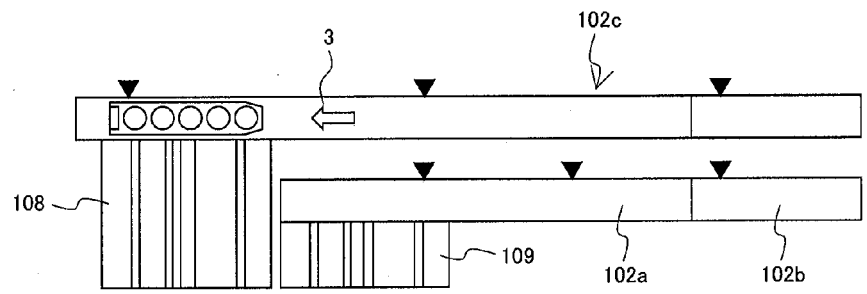
FIG. 45 is a diagram illustrating a state of the specimen container rack in the internal conveyance paths.
Figure 46:
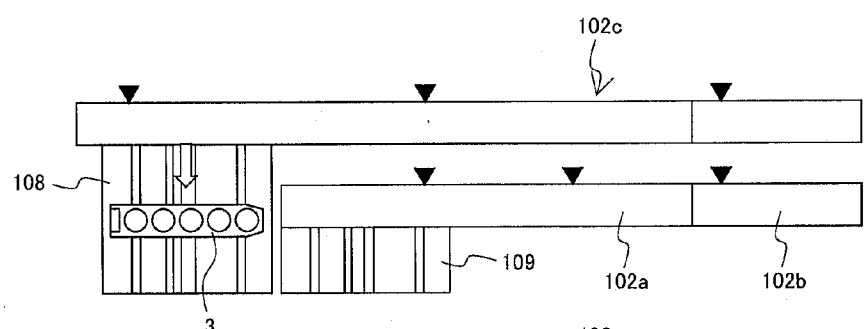
FIG. 46 is a diagram illustrating a state of the specimen container rack in the internal conveyance paths.
Figure 47:
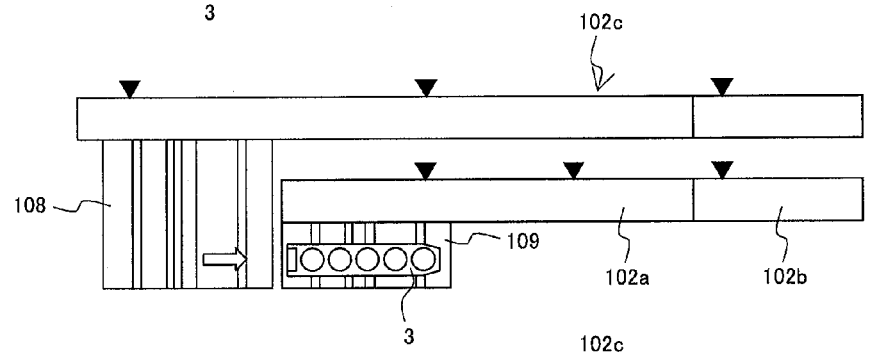
FIG. 47 is a diagram illustrating a state of the specimen container rack in the internal conveyance paths.

FIG. 43 is a diagram illustrating an entire configuration of the specimen container transfer mechanism part according to the fourth embodiment. FIGS. 44 to 48 are diagrams illustrating states in which the specimen container rack 3 is conveyed by internal conveyance paths 102a, 102b, 102c. Same reference signs are assigned to members identical to those in the first embodiment throughout the drawings, and descriptions thereof are omitted.

In FIG. 34, the internal conveyance path 102c which conveys the specimen container rack 3 from the analysis device 400 to an upstream side end part of the internal conveyance path 102a is disposed.

Figure 48:
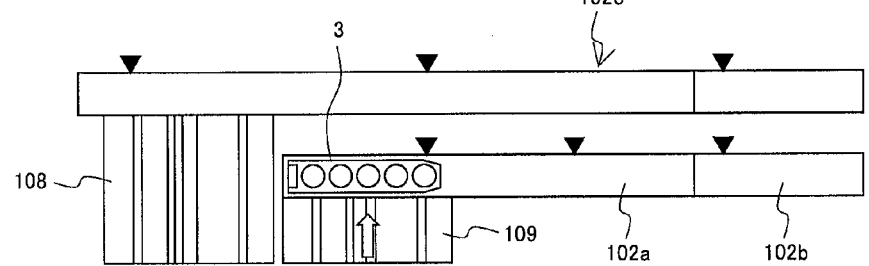
FIG. 48 is a diagram illustrating a state of the specimen container rack in the internal conveyance paths.

The internal conveyance path 102c is provided to bidirectionally convey and circulate the specimen container rack 3 between the specimen container transfer mechanism part 100 and the analysis device 400. The specimen container rack 3 is conveyed from the analysis device 400 by the internal conveyance path 102c (see FIG. 44). When arriving at a downstream side of the internal conveyance path 102c (i.e., an upstream side of the internal conveyance path 102a) (see FIG. 45), the specimen container rack 3 is carried into a rack holding lane 108 (see FIG. 46), is carried into a rack holding lane 109 from a downstream side of the rack holding lane 108 (see FIG. 47), and is carried out to the internal conveyance path 102a from an upstream side of the rack holding lane 109 (FIG. 48).

It should be noted that, when a rack 141 mounted with a specimen container 1 subjected to analysis processing in the analysis device 400 is carried out from the analysis system and returned to the transfer device, the specimen container 1 is extracted by a specimen container moving mechanism 104 and mounted on the empty specimen container holder 2 stopped by the stopper mechanism 106h, a bar code 1a and an RFID element 2a are similarly read, and next conveyance path information is constructed and conveyed by a control part 10.

Other configurations are similar to those in the first embodiment.

Effects similar to those in the first embodiment can be obtained in the present embodiment configured as described above.

Further, since it is no longer necessary to replenish the specimen container transfer mechanism part 100 with the empty specimen container rack 3, man-hours can be suppressed even in a facility handling a large amount of specimens, such as a large-scaled hospital or an examination center.

In the present embodiment, necessity of transfer is determined by the control part 10 based on information stored in the RFID element 2a. However, it may be configured that information including the necessity of transfer is stored in the RFID element 2a and that determination is made when reading the RFID element 2a.

<Variations of Fourth Embodiment>

Figure 49:
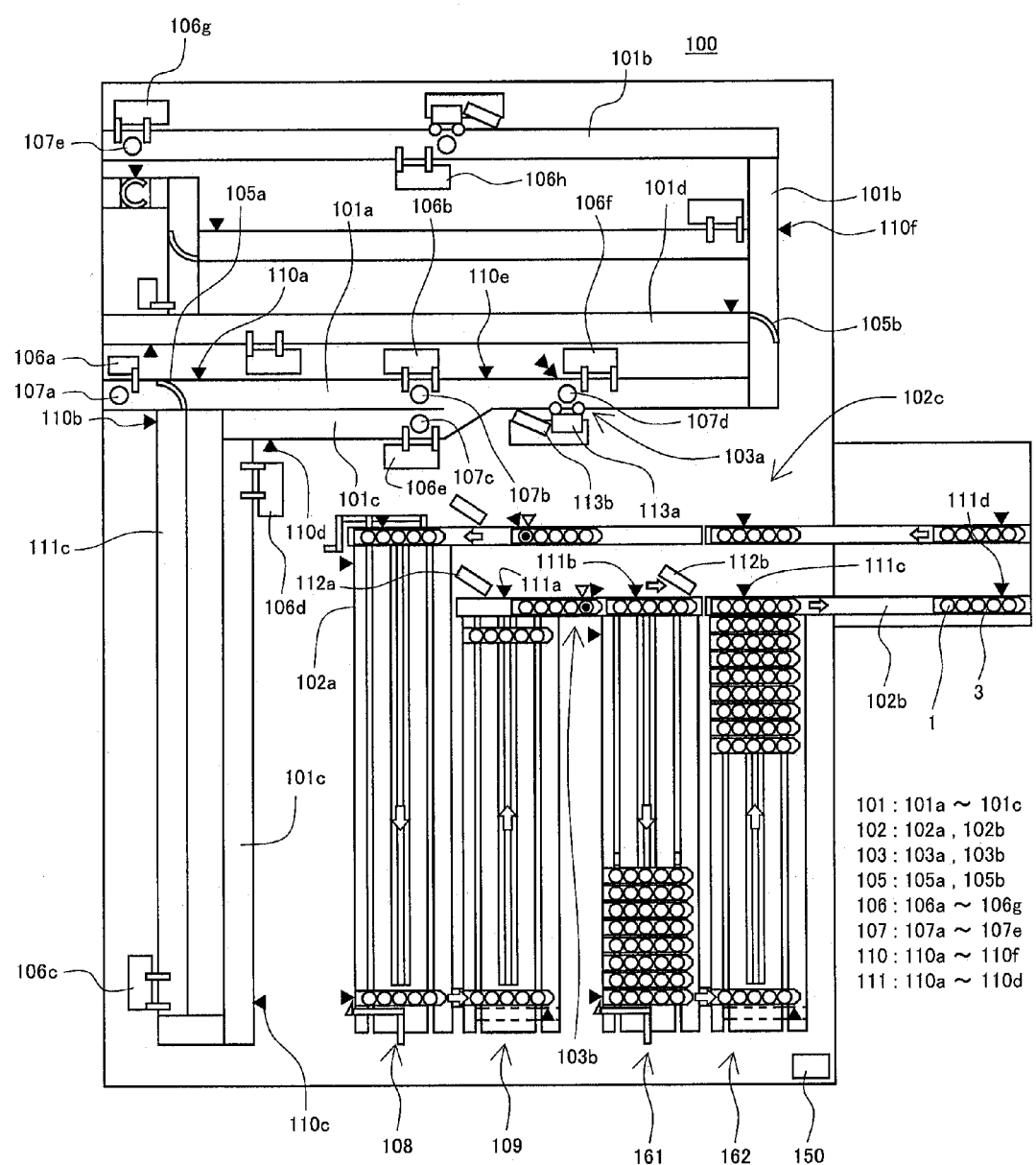
FIG. 49 is a diagram illustrating an entire configuration of a specimen container transfer mechanism part according to a variation of the fourth embodiment.
Figure 50:
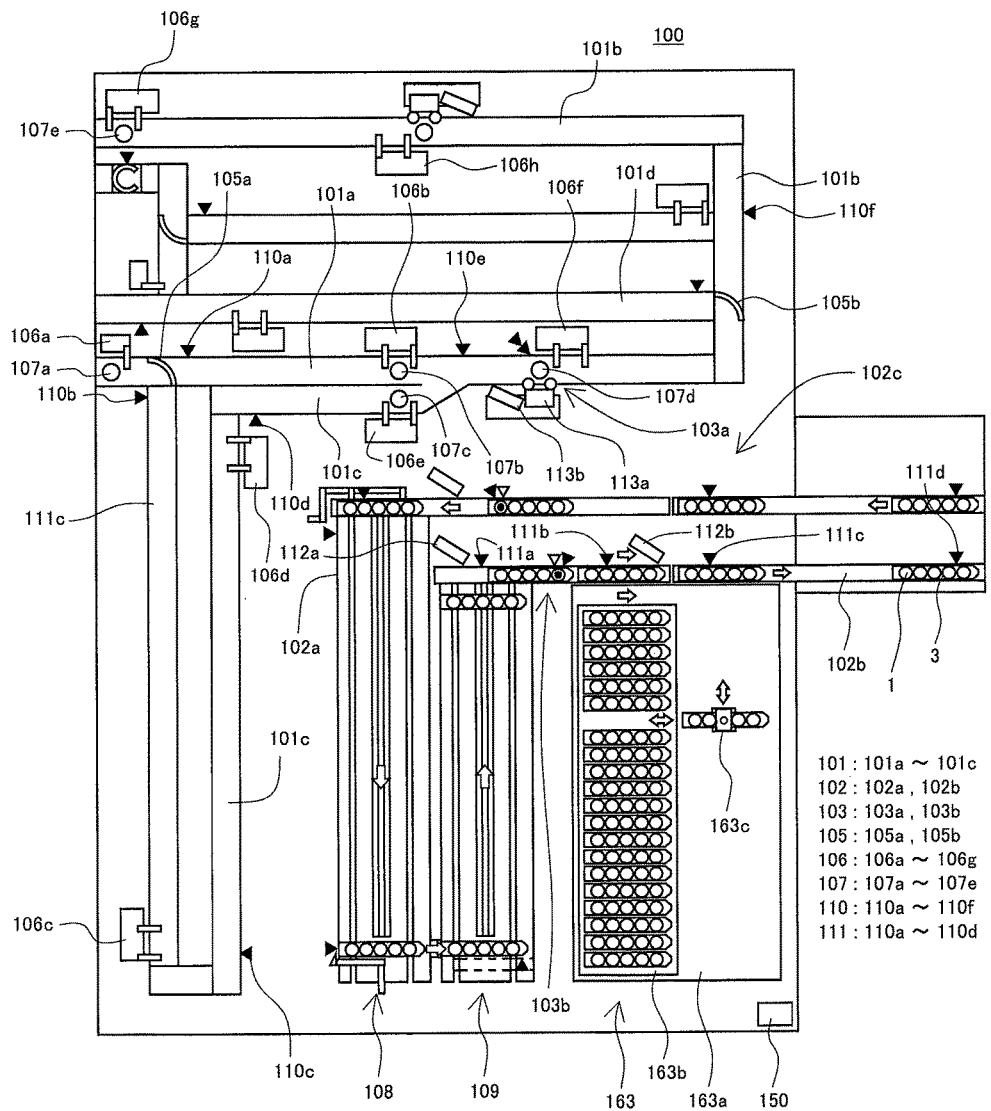
FIG. 50 is a diagram illustrating an entire configuration of a specimen container transfer mechanism part according to a variation of the fourth embodiment.

In the fourth embodiment, a case of using the rack holding lanes 108, 109 has been described as an example. However, the present invention is not limited to this. For example, as illustrated in FIG. 49, a case of using in combination the rack holding lanes 161, 162 with the sequential structures described in the second embodiment, or as illustrated in FIG. 50, a case of using in combination the rack holding lane 163 with the random access structure described in the third embodiment can be also considered.

In these cases as well, effects similar to those in the first embodiment and effects similar to those in the respective embodiments can be obtained.

REFERENCE SIGNS LIST 1 specimen container
1a bar code
1b specimen
2 specimen container holder (first carrier)
3 specimen container rack (second carrier)
10 control part
10a transfer control part
10b storage part
100, 200 specimen container transfer mechanism part
101, 102 internal conveyance path
103 specimen container transfer position
104 specimen container moving mechanism
105 internal conveyance path selection mechanism
106 stopper mechanism
107 RFID reader
108, 109 rack holding lane
110 holder detector
111 rack detector
112, 113b bar code reader
150 stop switch
161, 162, 163 rack holding lane
300 preprocessing device
400, 500 analysis device
600 conveyance path

The invention claimed is:

1. A specimen container transfer device to transfer a specimen container from a first carrier to a second carrier, and transport the second carrier to an analysis device, comprising:

a first conveyance path configured to convey the first carrier mounted with the specimen container to a first specimen container transfer position, the first conveyance path including a first internal conveyance path configured to convey the first carrier to the first specimen container transfer position and a second internal conveyance path configured to convey the first carrier to the first specimen container transfer position via a distance which is longer than the first internal conveyance path;

a second conveyance path separate from the first conveyance path and configured to convey the second carrier from a second specimen container transfer position to the analysis device as a conveyance destination;

a specimen chuck configured to grasp the specimen container from the first carrier at the first specimen container transfer position and transfer the specimen container to the second carrier at the second specimen container transfer position; and a controller configured to:
  determine whether the conveyance destination is in a state to receive the specimen container,
  upon determining that the conveyance destination is in the state to receive the specimen container, control the first carrier mounted with the specimen container to be conveyed in the first internal conveyance path to the first specimen container transfer position,
  upon determining that the conveyance destination is not in the state to receive the specimen container, control the first carrier mounted with the specimen container to be conveyed in the second internal conveyance path to the first specimen container transfer position,
  upon determining that the first carrier mounted with the specimen container is at the first specimen container transfer position, control the specimen chuck to grasp the specimen container mounted with the first carrier at the first specimen container transfer position and transfer the specimen container to the second carrier at the second specimen container transfer position, and
  upon determining that the second carrier mounted with the specimen container is at the second specimen container transfer position, control the second carrier mounted with the specimen container to be conveyed in the second conveyance path to the conveyance destination,
wherein the specimen container transfer device further comprises a carrier holding lane configured to hold a plurality of second carriers, including the second carrier, which are not mounted with the specimen container,
wherein the second conveyance path includes a third internal conveyance path, and a fourth internal conveyance path, each being individually driven such that conveyance of the second carrier on the third internal conveyance path is performed separately from conveyance of the second carrier on the fourth internal conveyance path, and
wherein the controller is further configured to:
  convey the second carrier to be conveyed from the carrier holding lane in the third internal conveyance path to the second specimen container transfer position, and
  convey the second carrier mounted with the specimen container to be conveyed from the second specimen container transfer position in the fourth internal conveyance path to the conveyance destination.

2. The specimen container transfer device according to claim 1, further comprising:
an internal conveyance path selection mechanism which selectively switches between the first internal conveyance path and the second internal conveyance path,
wherein the controller is further configured to control the internal conveyance path selection mechanism to direct the first carrier mounted with the specimen container to be conveyed in the first internal conveyance path or the second internal conveyance path based on conveyance information previously set to the specimen container mounted on the first carrier.

3. The specimen container transfer device according to claim 1, further comprising:
a carrier stopper provided in the second internal conveyance path and configured to temporarily hold and release the first carrier mounted with the specimen container in the second internal conveyance path,
wherein controller is further configured to control the carrier stopper based on conveyance information previously set to the specimen container mounted on the first carrier.

4. The specimen container transfer device according to claim 2, wherein the internal conveyance path selection mechanism switches between the first internal conveyance path and the second internal conveyance path based on priority of analysis.

5. The specimen container transfer device according to claim 1, wherein the first carrier is a holder consisting of a single location configured to mount the specimen container, and the second carrier is a rack including a plurality of locations configured to mount the specimen container.

6. A specimen processing system, comprising:
a preprocessing system configured to perform preprocessing on a specimen contained in a specimen container;
a plurality of analysis systems configured to perform analysis processing on the specimen, in the specimen container, subjected to the preprocessing;
a first conveyance path which conveys a first carrier mounted with the specimen container between the preprocessing system and the plurality of analysis systems; and
a plurality of specimen container transfer devices respectively connected to the plurality of analysis systems,
wherein each of the specimen container transfer devices respectively includes:
a second conveyance path connected to the first conveyance path and configured to convey the first carrier mounted with the specimen container to a first specimen container transfer position, the second conveyance path including a first internal conveyance path configured to convey the first carrier to the first specimen container transfer position and a second internal conveyance path configured to convey the first carrier to the first specimen container transfer position via a distance which is longer than the first internal conveyance path,
a third conveyance path separate from the first conveyance path and the second conveyance path and configured to convey a second carrier from a second specimen container transfer position to the respectively connected one of the analysis systems as a conveyance destination,
a specimen chuck configured to grasp the specimen container from the first carrier at the first specimen container transfer position and transfer the specimen container to the second carrier at the second specimen container transfer position; and
a controller configured to:
  determine whether the conveyance destination is in a state to receive the specimen container,
  upon determining that the conveyance destination is in the state to receive the specimen container, control the first carrier mounted with the specimen container to be conveyed in the first internal conveyance path to the first specimen container transfer position,
  upon determining that the conveyance destination is not in the state to receive the specimen container, control the first carrier mounted with the specimen container to be conveyed in the second internal conveyance path to the first specimen container transfer position, upon determining that the first carrier mounted with the specimen container is at the first specimen container transfer position, control the specimen chuck to grasp the specimen container mounted with the first carrier at the first specimen container transfer position and transfer the specimen container to the second carrier at the second specimen container transfer position, and upon determining that the second carrier mounted with the specimen container is at the second specimen container transfer position, control the second carrier mounted with the specimen container to be conveyed in the third conveyance path to the conveyance destination, wherein the specimen processing system further comprises a carrier holding lane configured to hold a plurality of second carriers, including the second carrier, which are not mounted with the specimen container, wherein the third conveyance path includes a third internal conveyance path, and a fourth internal conveyance path, each being individually driven such that the conveyance of the second carrier on the third internal conveyance path is performed separately from conveyance of the second carrier on the fourth internal conveyance path, and wherein the controller is further configured to:
  convey the second carrier to be conveyed from the carrier holding lane in the third internal conveyance path to the second specimen container transfer position, and
  convey the second carrier mounted with the specimen container to be conveyed from the second specimen container transfer position in the fourth internal conveyance path to the conveyance destination.

7. The specimen processing system according to claim 6, wherein each of the specimen container transfer devices further includes:
  an internal conveyance path selection mechanism which selectively switches between the first internal conveyance path and the second internal conveyance path, and
  wherein the controller is further configured to control the internal conveyance path selection mechanism to direct the first carrier mounted with the specimen container to be conveyed in the first internal conveyance path or the second internal conveyance path based on conveyance information previously set to the specimen container mounted on the first carrier.

8. The specimen processing system according to claim 6, wherein the first carrier is a holder consisting of a single location configured to mount the specimen container, and the second carrier is a rack including a plurality of locations configured to mount the specimen container.

* * * * *